(12) United States Patent
Kaiser et al.

(10) Patent No.: US 8,506,597 B2
(45) Date of Patent: Aug. 13, 2013

(54) METHOD AND APPARATUS FOR INTEROSSEOUS MEMBRANE RECONSTRUCTION

(75) Inventors: Ryan A. Kaiser, Leesburg, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 13/281,016

(22) Filed: Oct. 25, 2011

(65) Prior Publication Data

US 2013/0103082 A1    Apr. 25, 2013

(51) Int. Cl.
 *A61B 17/04* (2006.01)
 *A61B 17/84* (2006.01)
 *A61F 2/08* (2006.01)

(52) U.S. Cl.
 USPC .......................................... 606/232; 606/300

(58) Field of Classification Search
 USPC .................. 606/232, 300; 623/13.11, 13.14, 623/13.19, 13.2, 20.32
 See application file for complete search history.

(56) References Cited

U.S. PATENT DOCUMENTS

| | | | |
|---|---|---|---|
| 65,499 A | 6/1867 | Miller | |
| 126,366 A | 4/1872 | Wills | |
| 233,475 A | 10/1880 | Cook et al. | |
| 261,501 A | 7/1882 | Vandermark | |
| 268,407 A | 12/1882 | Hughes | |
| 417,805 A | 12/1889 | Beaman | |
| 487,304 A | 12/1892 | Todd | |
| 762,710 A | 6/1901 | Hall | |
| 837,767 A | 12/1906 | Aims | |
| 838,203 A | 12/1906 | Neil | |
| 1,059,631 A | 4/1913 | Popovics | |
| 1,131,155 A | 3/1915 | Murphy | |
| 1,153,450 A | 9/1915 | Schaff | |
| 1,346,940 A | 7/1920 | Collins | |
| 1,635,066 A | 7/1927 | Wells | |
| 401,677 A | 11/1933 | Hans | |
| 1,950,799 A | 3/1934 | Jones | |
| 2,065,659 A | 12/1936 | Cullen | |
| 2,108,206 A | 2/1938 | Meeker | |
| 2,121,193 A | 6/1938 | Hanicke | |
| 2,242,003 A | 5/1941 | Lorenzo | |
| 2,267,925 A | 12/1941 | Johnston | |
| 2,302,986 A | 11/1942 | Vollrath | |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

"AperFix® System Surgical Technique Guide. Single Tunnel Double Bundle.™" Cayenne Medical brochure. (Aug. 2008) 8 sheets.

(Continued)

*Primary Examiner* — Dianne Dornbusch
(74) *Attorney, Agent, or Firm* — Harness, Dickey

(57) ABSTRACT

A method for repairing a defect in an interosseous membrane located between a first bone and a second bone. The method includes: coupling a flexible member to the first bone and the second bone, the flexible member extending past a first area of the interosseous membrane between the first bone and the second bone; and orienting the flexible member such that the flexible member extends generally parallel to fibers of the first area of the interosseous membrane.

18 Claims, 8 Drawing Sheets

(56) References Cited

U.S. PATENT DOCUMENTS

| | | |
|---|---|---|
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |

| | | |
|---|---|---|
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee |
| 4,784,126 A | 11/1988 | Hourahane |
| 4,787,882 A | 11/1988 | Claren |
| 4,790,297 A | 12/1988 | Luque |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,030,235 A | 7/1991 | Campbell, Jr. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |

| | | | | | | |
|---|---|---|---|---|---|---|
| 5,123,913 | A | 6/1992 | Wilk et al. | 5,342,369 A | 8/1994 | Harryman, II |
| 5,123,914 | A | 6/1992 | Cope | 5,346,462 A | 9/1994 | Barber |
| 5,127,785 | A | 7/1992 | Faucher et al. | 5,354,298 A | 10/1994 | Lee et al. |
| 5,129,901 | A | 7/1992 | Decoste | 5,356,412 A | 10/1994 | Golds et al. |
| 5,129,902 | A | 7/1992 | Goble et al. | 5,356,413 A | 10/1994 | Martins et al. |
| 5,129,904 | A | 7/1992 | Illi et al. | 5,356,417 A | 10/1994 | Golds |
| 5,129,906 | A | 7/1992 | Ross et al. | 5,358,511 A | 10/1994 | Gatturna et al. |
| 5,139,498 | A | 8/1992 | Astudillo Ley | 5,360,431 A | 11/1994 | Puno et al. |
| 5,139,499 | A | 8/1992 | Small et al. | 5,362,294 A | 11/1994 | Seitzinger |
| 5,139,520 | A | 8/1992 | Rosenberg | 5,364,400 A | 11/1994 | Rego, Jr. et al. |
| 5,143,498 | A | 9/1992 | Whitman | 5,366,461 A | 11/1994 | Blasnik |
| 5,147,362 | A | 9/1992 | Goble | 5,368,599 A | 11/1994 | Hirsch et al. |
| 5,149,329 | A | 9/1992 | Richardson | 5,370,661 A | 12/1994 | Branch |
| 5,152,790 | A | 10/1992 | Rosenberg et al. | 5,370,662 A | 12/1994 | Stone et al. |
| 5,154,189 | A | 10/1992 | Oberlander | 5,372,146 A | 12/1994 | Branch |
| 5,156,616 | A | 10/1992 | Meadows et al. | 5,372,604 A | 12/1994 | Trott |
| 5,163,960 | A | 11/1992 | Bonutti | 5,372,821 A | 12/1994 | Badylak et al. |
| D331,626 | S | 12/1992 | Hayhurst et al. | 5,374,268 A | 12/1994 | Sander |
| 5,169,400 | A | 12/1992 | Muhling et al. | 5,379,492 A | 1/1995 | Glesser |
| 5,176,682 | A | 1/1993 | Chow | 5,383,878 A | 1/1995 | Roger et al. |
| 5,178,629 | A | 1/1993 | Kammerer | 5,383,904 A | 1/1995 | Totakura et al. |
| 5,183,458 | A | 2/1993 | Marx | 5,391,171 A | 2/1995 | Schmieding |
| 5,192,282 | A | 3/1993 | Draenert et al. | 5,391,176 A | 2/1995 | de la Torre |
| 5,197,987 | A | 3/1993 | Koch et al. | 5,391,182 A | 2/1995 | Chin |
| 5,203,784 | A | 4/1993 | Ross et al. | 5,393,302 A | 2/1995 | Clark et al. |
| 5,203,787 | A | 4/1993 | Noblitt et al. | RE34,871 E | 3/1995 | McGuire et al. |
| 5,207,679 | A | 5/1993 | Li | 5,397,356 A | 3/1995 | Goble et al. |
| 5,209,753 | A | 5/1993 | Biedermann et al. | 5,403,328 A | 4/1995 | Shallman |
| 5,209,805 | A | 5/1993 | Spraggins | 5,403,329 A | 4/1995 | Hinchcliffe |
| 5,211,647 | A | 5/1993 | Schmieding | 5,403,348 A | 4/1995 | Bonutti |
| 5,211,650 | A | 5/1993 | Noda | 5,405,359 A | 4/1995 | Pierce |
| 5,214,987 | A | 6/1993 | Fenton, Sr. | 5,417,691 A | 5/1995 | Hayhurst |
| 5,219,359 | A | 6/1993 | McQuilkin et al. | 5,417,698 A | 5/1995 | Green et al. |
| 5,222,976 | A | 6/1993 | Yoon | 5,417,712 A | 5/1995 | Whittaker et al. |
| 5,224,946 | A | 7/1993 | Hayhurst et al. | 5,423,819 A | 6/1995 | Small et al. |
| 5,230,699 | A | 7/1993 | Grasinger | 5,423,821 A | 6/1995 | Pasque |
| 5,232,436 | A | 8/1993 | Janevski | 5,423,823 A | 6/1995 | Schmieding |
| 5,234,435 | A | 8/1993 | Seagrave, Jr. | 5,423,860 A | 6/1995 | Lizardi et al. |
| 5,235,238 | A | 8/1993 | Nomura et al. | 5,425,733 A | 6/1995 | Schmieding |
| 5,236,445 | A | 8/1993 | Hayhurst et al. | 5,425,766 A | 6/1995 | Bowald et al. |
| 5,236,461 | A | 8/1993 | Forte | 5,433,751 A | 7/1995 | Christel et al. |
| 5,242,447 | A | 9/1993 | Borzone | 5,437,680 A | 8/1995 | Yoon |
| 5,246,441 | A | 9/1993 | Ross et al. | 5,437,685 A | 8/1995 | Blasnik |
| 5,249,899 | A | 10/1993 | Wilson | 5,439,684 A | 8/1995 | Prewett et al. |
| 5,250,053 | A | 10/1993 | Snyder | 5,441,508 A | 8/1995 | Gazielly et al. |
| 5,258,015 | A | 11/1993 | Li et al. | 5,443,468 A | 8/1995 | Johnson |
| 5,258,016 | A | 11/1993 | DiPoto et al. | 5,443,482 A | 8/1995 | Stone et al. |
| 5,258,040 | A | 11/1993 | Bruchman et al. | 5,443,483 A | 8/1995 | Kirsch et al. |
| 5,261,908 | A | 11/1993 | Campbell, Jr. | 5,443,509 A | 8/1995 | Boucher et al. |
| 5,268,001 | A | 12/1993 | Nicholson et al. | 5,445,833 A | 8/1995 | Badylak et al. |
| 5,269,160 | A | 12/1993 | Wood | 5,447,512 A | 9/1995 | Wilson et al. |
| 5,269,783 | A | 12/1993 | Sander | 5,449,361 A | 9/1995 | Preissman |
| 5,269,806 | A | 12/1993 | Sardelis et al. | 5,451,203 A | 9/1995 | Lamb |
| 5,269,809 | A | 12/1993 | Hayhurst et al. | 5,454,811 A | 10/1995 | Huebner |
| 5,279,311 | A | 1/1994 | Snyder | 5,454,821 A | 10/1995 | Harm et al. |
| 5,281,422 | A | 1/1994 | Badylak et al. | 5,456,685 A | 10/1995 | Huebner |
| 5,282,809 | A | 2/1994 | Kammerer et al. | 5,456,722 A | 10/1995 | McLeod et al. |
| 5,282,832 | A | 2/1994 | Toso et al. | 5,458,601 A | 10/1995 | Young, Jr. et al. |
| 5,282,867 | A | 2/1994 | Mikhail | 5,458,604 A | 10/1995 | Schmieding |
| 5,285,040 | A | 2/1994 | Brandberg et al. | 5,462,542 A | 10/1995 | Alesi, Jr. |
| 5,290,217 | A | 3/1994 | Campos | 5,462,560 A | 10/1995 | Stevens |
| 5,306,301 | A | 4/1994 | Graf et al. | 5,464,426 A | 11/1995 | Bonutti |
| 5,312,422 | A | 5/1994 | Trott | 5,464,427 A | 11/1995 | Curtis et al. |
| 5,312,438 | A | 5/1994 | Johnson | 5,464,440 A | 11/1995 | Johansson et al. |
| 5,318,566 | A | 6/1994 | Miller | 5,466,237 A | 11/1995 | Byrd, III et al. |
| 5,318,575 | A | 6/1994 | Chesterfield et al. | 5,467,786 A | 11/1995 | Allen et al. |
| 5,318,577 | A | 6/1994 | Li | 5,470,334 A | 11/1995 | Ross et al. |
| 5,318,578 | A | 6/1994 | Hasson | 5,470,337 A | 11/1995 | Moss |
| 5,320,115 | A | 6/1994 | Kenna | 5,470,338 A | 11/1995 | Whitfield et al. |
| 5,320,626 | A | 6/1994 | Schmieding | 5,472,452 A | 12/1995 | Trott |
| 5,320,633 | A | 6/1994 | Allen et al. | 5,474,565 A | 12/1995 | Trott |
| 5,324,308 | A | 6/1994 | Pierce | 5,474,568 A | 12/1995 | Scott |
| 5,330,489 | A | 7/1994 | Green et al. | 5,474,572 A | 12/1995 | Hayhurst |
| 5,333,625 | A | 8/1994 | Klein | 5,478,344 A | 12/1995 | Stone et al. |
| 5,334,204 | A | 8/1994 | Clewett et al. | 5,478,345 A | 12/1995 | Stone et al. |
| 5,336,229 | A | 8/1994 | Noda | 5,480,403 A | 1/1996 | Lee et al. |
| 5,336,231 | A | 8/1994 | Adair | 5,480,406 A | 1/1996 | Nolan et al. |
| 5,336,240 | A | 8/1994 | Metzler et al. | 5,484,442 A | 1/1996 | Melker et al. |
| 5,339,870 | A | 8/1994 | Green et al. | 5,486,197 A | 1/1996 | Le et al. |

| Patent No. | Date | Name |
|---|---|---|
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,736 A | 4/1996 | Reimels et al. |
| 5,507,754 A | 4/1996 | Green et al. |
| 5,520,691 A | 5/1996 | Branch |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,571,090 A | 11/1996 | Sherts |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,419 A | 11/1997 | Thal |
| 5,688,285 A | 11/1997 | Yamada |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,711,969 A | 1/1998 | Patel et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Br.ang.nemark et al. |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,915 A | 8/1998 | Pierson, III et al. |

| | | | | | | |
|---|---|---|---|---|---|---|
| 5,797,916 | A | 8/1998 | McDowell | 5,989,282 | A | 11/1999 | Bonutti |
| 5,797,928 | A | 8/1998 | Kogasaka | 5,993,452 | A | 11/1999 | Vandewalle |
| 5,800,407 | A | 9/1998 | Eldor et al. | 5,993,476 | A | 11/1999 | Groiso |
| 5,810,824 | A | 9/1998 | Chan | 5,997,542 | A | 12/1999 | Burke |
| 5,810,848 | A | 9/1998 | Hayhurst | 5,997,552 | A | 12/1999 | Person et al. |
| 5,814,069 | A | 9/1998 | Schulze et al. | 5,997,575 | A | 12/1999 | Whitson et al. |
| 5,814,070 | A | 9/1998 | Borzone et al. | 6,001,100 | A | 12/1999 | Sherman et al. |
| 5,814,072 | A | 9/1998 | Bonutti | 6,007,538 | A | 12/1999 | Levin |
| 5,814,073 | A | 9/1998 | Bonutti | 6,007,567 | A | 12/1999 | Bonutti |
| 5,823,980 | A | 10/1998 | Kopfer | 6,010,525 | A | 1/2000 | Bonutti et al. |
| 5,824,011 | A | 10/1998 | Stone et al. | 6,016,727 | A | 1/2000 | Morgan |
| 5,830,234 | A | 11/1998 | Wojciechowicz et al. | 6,022,352 | A | 2/2000 | Vandewalle |
| 5,843,084 | A | 12/1998 | Hart et al. | 6,022,373 | A | 2/2000 | Li |
| 5,845,645 | A | 12/1998 | Bonutti | 6,024,758 | A | 2/2000 | Thal |
| 5,846,254 | A | 12/1998 | Schulze et al. | 6,027,523 | A | 2/2000 | Schmieding |
| 5,848,983 | A | 12/1998 | Basaj et al. | 6,030,410 | A | 2/2000 | Zurbrugg |
| 5,849,012 | A | 12/1998 | Abboudi | 6,033,429 | A | 3/2000 | Magovern |
| 5,860,973 | A | 1/1999 | Michelson | 6,033,430 | A | 3/2000 | Bonutti |
| 5,868,740 | A | 2/1999 | LeVeen et al. | 6,039,753 | A | 3/2000 | Meislin |
| 5,868,748 | A | 2/1999 | Burke | 6,041,485 | A | 3/2000 | Pedlick et al. |
| 5,868,789 | A | 2/1999 | Huebner | 6,042,601 | A | 3/2000 | Smith |
| 5,871,484 | A | 2/1999 | Spievack et al. | 6,045,551 | A | 4/2000 | Bonutti |
| 5,871,486 | A | 2/1999 | Huebner et al. | 6,045,571 | A | 4/2000 | Hill et al. |
| 5,871,490 | A | 2/1999 | Schulze et al. | 6,045,572 | A | 4/2000 | Johnson et al. |
| 5,885,294 | A | 3/1999 | Pedlick et al. | 6,045,573 | A | 4/2000 | Wenstrom, Jr. et al. |
| 5,891,168 | A | 4/1999 | Thal | 6,045,574 | A | 4/2000 | Thal |
| 5,893,592 | A | 4/1999 | Schulze et al. | 6,047,826 | A | 4/2000 | Kalinski et al. |
| 5,895,395 | A | 4/1999 | Yeung | 6,048,343 | A | 4/2000 | Mathis et al. |
| 5,897,564 | A | 4/1999 | Schulze et al. | 6,051,006 | A | 4/2000 | Shluzas et al. |
| 5,897,574 | A | 4/1999 | Bonutti | 6,051,007 | A | 4/2000 | Hogendijk et al. |
| 5,899,902 | A | 5/1999 | Brown et al. | 6,053,916 | A | 4/2000 | Moore |
| 5,899,938 | A | 5/1999 | Sklar et al. | 6,053,921 | A | 4/2000 | Wagner et al. |
| 5,908,421 | A | 6/1999 | Beger et al. | 6,056,752 | A | 5/2000 | Roger |
| 5,908,436 | A | 6/1999 | Cuschieri et al. | 6,056,772 | A | 5/2000 | Bonutti |
| 5,910,148 | A | 6/1999 | Reimels et al. | 6,056,773 | A | 5/2000 | Bonutti |
| 5,911,721 | A | 6/1999 | Nicholson et al. | 6,059,817 | A | 5/2000 | Bonutti et al. |
| 5,918,604 | A | 7/1999 | Whelan | 6,059,818 | A | 5/2000 | Johnson et al. |
| 5,921,986 | A | 7/1999 | Bonutti | 6,062,344 | A | 5/2000 | Okabe et al. |
| 5,925,008 | A | 7/1999 | Douglas | 6,068,648 | A | 5/2000 | Cole et al. |
| 5,928,231 | A | 7/1999 | Klein et al. | 6,071,305 | A | 6/2000 | Brown et al. |
| 5,928,267 | A | 7/1999 | Bonutti et al. | 6,074,403 | A | 6/2000 | Nord |
| RE36,289 | E | 8/1999 | Le et al. | 6,077,277 | A | 6/2000 | Mollenauer et al. |
| 5,931,838 | A | 8/1999 | Vito | 6,077,292 | A | 6/2000 | Bonutti |
| 5,931,844 | A | 8/1999 | Thompson et al. | 6,080,185 | A | 6/2000 | Johnson et al. |
| 5,931,869 | A | 8/1999 | Boucher et al. | 6,086,591 | A | 7/2000 | Bojarski |
| 5,935,119 | A | 8/1999 | Guy et al. | 6,086,592 | A | 7/2000 | Rosenberg et al. |
| 5,935,133 | A | 8/1999 | Wagner et al. | 6,086,608 | A | 7/2000 | Ek et al. |
| 5,935,149 | A | 8/1999 | Ek | 6,093,200 | A | 7/2000 | Liu et al. |
| 5,938,668 | A | 8/1999 | Scirica et al. | 6,096,060 | A | 8/2000 | Fitts et al. |
| 5,941,439 | A | 8/1999 | Kammerer et al. | 6,099,527 | A | 8/2000 | Hochschuler et al. |
| 5,941,900 | A | 8/1999 | Bonutti | 6,099,530 | A | 8/2000 | Simonian et al. |
| 5,944,739 | A | 8/1999 | Zlock et al. | 6,099,568 | A | 8/2000 | Simonian et al. |
| 5,946,783 | A | 9/1999 | Plociennik et al. | 6,106,545 | A | 8/2000 | Egan |
| 5,947,915 | A | 9/1999 | Thibodo, Jr. | 6,110,128 | A | 8/2000 | Andelin et al. |
| 5,947,982 | A | 9/1999 | Duran | 6,117,160 | A | 9/2000 | Bonutti |
| 5,947,999 | A | 9/1999 | Groiso | 6,117,162 | A | 9/2000 | Schmieding et al. |
| 5,948,002 | A | 9/1999 | Bonutti | 6,123,710 | A | 9/2000 | Pinczewski et al. |
| 5,951,559 | A | 9/1999 | Burkhart | 6,132,433 | A | 10/2000 | Whelan |
| 5,951,560 | A | 9/1999 | Simon et al. | 6,132,437 | A | 10/2000 | Omurtag et al. |
| 5,954,747 | A | 9/1999 | Clark | 6,139,565 | A | 10/2000 | Stone et al. |
| 5,957,953 | A | 9/1999 | DiPoto et al. | RE36,974 | E | 11/2000 | Bonutti |
| 5,961,521 | A | 10/1999 | Roger et al. | 6,143,017 | A | 11/2000 | Thal |
| 5,961,524 | A | 10/1999 | Crombie | 6,146,406 | A | 11/2000 | Shluzas et al. |
| 5,964,764 | A | 10/1999 | West, Jr. et al. | 6,146,408 | A | 11/2000 | Bartlett |
| 5,964,767 | A | 10/1999 | Tapia et al. | 6,149,653 | A | 11/2000 | Deslauriers |
| 5,964,769 | A | 10/1999 | Wagner et al. | 6,149,669 | A | 11/2000 | Li |
| 5,964,783 | A | 10/1999 | Grafton et al. | 6,152,928 | A | 11/2000 | Wenstrom, Jr. |
| 5,968,045 | A | 10/1999 | Frazier | 6,152,934 | A | 11/2000 | Harper et al. |
| 5,968,047 | A | 10/1999 | Reed | 6,152,936 | A | 11/2000 | Christy et al. |
| 5,968,077 | A | 10/1999 | Wojciechowicz et al. | 6,152,949 | A | 11/2000 | Bonutti |
| 5,972,006 | A | 10/1999 | Sciaino, Jr. | 6,156,039 | A | 12/2000 | Thal |
| 5,976,125 | A | 11/1999 | Graham | 6,156,056 | A | 12/2000 | Kearns et al. |
| 5,976,127 | A | 11/1999 | Lax | 6,159,234 | A | 12/2000 | Bonutti et al. |
| 5,980,524 | A | 11/1999 | Justin et al. | 6,165,203 | A | 12/2000 | Krebs |
| 5,980,539 | A | 11/1999 | Kontos | 6,168,598 | B1 | 1/2001 | Martello |
| 5,980,558 | A | 11/1999 | Wiley | 6,168,628 | B1 | 1/2001 | Huebner |
| 5,980,559 | A | 11/1999 | Bonutti | 6,179,840 | B1 | 1/2001 | Bowman |
| 5,989,252 | A | 11/1999 | Fumex | 6,183,461 | B1 | 2/2001 | Matsuura et al. |
| 5,989,256 | A | 11/1999 | Kuslich et al. | 6,187,025 | B1 | 2/2001 | Machek |

| Patent No. | Date | Inventor(s) |
|---|---|---|
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,450 B2 | 11/2003 | Neisz et al. |
| 6,652,562 B2 | 11/2003 | Collier et al. |

| Patent | Type | Date | Inventor(s) |
|---|---|---|---|
| 6,652,563 | B2 | 11/2003 | Dreyfuss |
| 6,656,182 | B1 | 12/2003 | Hayhurst |
| 6,656,183 | B2 | 12/2003 | Colleran et al. |
| 6,658,182 | B1 | 12/2003 | Gonthier et al. |
| 6,660,008 | B1 | 12/2003 | Foerster et al. |
| 6,660,022 | B1 | 12/2003 | Li et al. |
| 6,663,634 | B2 | 12/2003 | Ahrens et al. |
| 6,663,656 | B2 | 12/2003 | Schmieding et al. |
| 6,666,868 | B2 | 12/2003 | Fallin |
| 6,682,533 | B1 | 1/2004 | Dinsdale et al. |
| 6,682,549 | B2 | 1/2004 | Bartlett |
| 6,685,728 | B2 | 2/2004 | Sinnott et al. |
| 6,689,137 | B2 | 2/2004 | Reed |
| 6,689,153 | B1 | 2/2004 | Skiba |
| 6,689,154 | B2 | 2/2004 | Bartlett |
| 6,692,499 | B2 | 2/2004 | Tormala et al. |
| 6,692,516 | B2 | 2/2004 | West, Jr. et al. |
| 6,712,849 | B2 | 3/2004 | Re et al. |
| 6,716,224 | B2 | 4/2004 | Singhatat |
| 6,716,957 | B2 | 4/2004 | Tunc |
| 6,730,092 | B2 | 5/2004 | Songer |
| 6,730,124 | B2 | 5/2004 | Steiner |
| 6,736,799 | B1 | 5/2004 | Erbe et al. |
| 6,737,053 | B1 | 5/2004 | Goh et al. |
| 6,746,483 | B1 | 6/2004 | Bojarski et al. |
| 6,752,810 | B1 | 6/2004 | Gao et al. |
| 6,752,831 | B2 | 6/2004 | Sybert et al. |
| 6,755,836 | B1 | 6/2004 | Lewis |
| 6,761,739 | B2 | 7/2004 | Shepard |
| 6,767,037 | B2 | 7/2004 | Wenstrom, Jr. |
| 6,770,076 | B2 | 8/2004 | Foerster |
| 6,770,084 | B1 | 8/2004 | Bain et al. |
| 6,773,450 | B2 | 8/2004 | Leung et al. |
| 6,779,701 | B2 | 8/2004 | Bailly et al. |
| 6,780,190 | B2 | 8/2004 | Maroney |
| 6,780,198 | B1 | 8/2004 | Gregoire et al. |
| 6,802,862 | B1 | 10/2004 | Roger et al. |
| 6,808,502 | B2 | 10/2004 | Nguyen et al. |
| 6,808,526 | B1 | 10/2004 | Magerl et al. |
| 6,814,741 | B2 | 11/2004 | Bowman et al. |
| 6,830,572 | B2 | 12/2004 | McDevitt et al. |
| 6,833,005 | B1 | 12/2004 | Mantas et al. |
| 6,840,953 | B2 | 1/2005 | Martinek |
| 6,860,885 | B2 | 3/2005 | Bonutti |
| 6,863,671 | B1 | 3/2005 | Strobel et al. |
| 6,872,040 | B2 | 3/2005 | Deeg et al. |
| 6,872,210 | B2 | 3/2005 | Hearn |
| 6,875,216 | B2 | 4/2005 | Wolf |
| 6,884,249 | B2 | 4/2005 | May et al. |
| 6,887,259 | B2 | 5/2005 | Lizardi |
| 6,890,354 | B2 | 5/2005 | Steiner et al. |
| 6,893,448 | B2 | 5/2005 | O'Quinn et al. |
| 6,896,686 | B2 | 5/2005 | Weber |
| 6,899,722 | B2 | 5/2005 | Bonutti |
| 6,902,573 | B2 | 6/2005 | Strobel et al. |
| 6,905,513 | B1 | 6/2005 | Metzger |
| 6,908,466 | B1 | 6/2005 | Bonutti et al. |
| 6,916,292 | B2 | 7/2005 | Morawski et al. |
| 6,916,321 | B2 | 7/2005 | TenHuisen et al. |
| 6,921,402 | B2 | 7/2005 | Contiliano et al. |
| 6,923,823 | B1 | 8/2005 | Bartlett et al. |
| 6,923,824 | B2 | 8/2005 | Morgan et al. |
| 6,951,565 | B2 | 10/2005 | Keane et al. |
| 6,966,887 | B1 | 11/2005 | Chin |
| 6,966,916 | B2 | 11/2005 | Kumar |
| 6,969,391 | B1 | 11/2005 | Gazzani |
| 6,969,398 | B2 | 11/2005 | Stevens et al. |
| 6,972,027 | B2 | 12/2005 | Fallin et al. |
| 6,980,903 | B2 | 12/2005 | Daniels et al. |
| 6,986,781 | B2 | 1/2006 | Smith |
| 6,989,034 | B2 | 1/2006 | Hammer et al. |
| 7,001,429 | B2 | 2/2006 | Ferguson |
| 7,004,959 | B2 | 2/2006 | Bonutti |
| 7,048,754 | B2 | 5/2006 | Martin et al. |
| 7,052,499 | B2 | 5/2006 | Steger et al. |
| 7,066,942 | B2 | 6/2006 | Treace |
| 7,066,944 | B2 | 6/2006 | Laufer et al. |
| 7,081,126 | B2 | 7/2006 | McDevitt et al. |
| 7,087,064 | B1 | 8/2006 | Hyde |
| 7,105,010 | B2 | 9/2006 | Hart et al. |
| 7,112,221 | B2 | 9/2006 | Harris et al. |
| 7,118,583 | B2 | 10/2006 | O'Quinn et al. |
| 7,131,467 | B2 | 11/2006 | Gao et al. |
| 7,137,996 | B2 | 11/2006 | Steiner et al. |
| 7,141,066 | B2 | 11/2006 | Steiner et al. |
| 7,144,414 | B2 | 12/2006 | Harvie et al. |
| 7,153,127 | B2 | 12/2006 | Struble et al. |
| 7,153,307 | B2 | 12/2006 | Scribner et al. |
| 7,153,312 | B1 | 12/2006 | Torrie et al. |
| 7,153,327 | B1 | 12/2006 | Metzger |
| 7,160,333 | B2 | 1/2007 | Plouhar et al. |
| 7,201,722 | B2 | 4/2007 | Krueger |
| 7,255,675 | B2 | 8/2007 | Gertner et al. |
| 7,255,715 | B2 | 8/2007 | Metzger |
| 7,261,716 | B2 | 8/2007 | Strobel et al. |
| 7,264,634 | B2 | 9/2007 | Schmieding |
| 7,285,124 | B2 | 10/2007 | Foerster |
| 7,303,577 | B1 | 12/2007 | Dean |
| 7,306,417 | B2 | 12/2007 | Dorstewitz |
| 7,326,222 | B2 | 2/2008 | Dreyfuss et al. |
| 7,329,272 | B2 | 2/2008 | Burkhart et al. |
| 7,361,179 | B2 | 4/2008 | Rousseau et al. |
| 7,377,845 | B2 | 5/2008 | Stewart et al. |
| 7,390,329 | B2 | 6/2008 | Westra et al. |
| 7,390,332 | B2 | 6/2008 | Selvitelli et al. |
| 7,399,018 | B1 | 7/2008 | Khachaturian |
| 7,442,210 | B2 | 10/2008 | Segal et al. |
| 7,465,308 | B2 | 12/2008 | Sikora et al. |
| 7,494,506 | B2 | 2/2009 | Brulez et al. |
| 7,513,910 | B2 | 4/2009 | Buskirk et al. |
| 7,578,825 | B2 | 8/2009 | Huebner |
| 7,585,311 | B2 | 9/2009 | Green et al. |
| 7,601,165 | B2 | 10/2009 | Stone |
| 7,608,092 | B1 | 10/2009 | Schaffhausen |
| 7,608,098 | B1 | 10/2009 | Stone et al. |
| 7,615,076 | B2 | 11/2009 | Cauthen, III et al. |
| 7,632,287 | B2 | 12/2009 | Baker et al. |
| 7,651,509 | B2 | 1/2010 | Bojarski et al. |
| 7,658,750 | B2 | 2/2010 | Li |
| 7,658,751 | B2 | 2/2010 | Stone et al. |
| 7,670,279 | B2 | 3/2010 | Gertner |
| 7,678,123 | B2 | 3/2010 | Chanduszko |
| 7,695,493 | B2 | 4/2010 | Saadat et al. |
| 7,736,379 | B2 | 6/2010 | Ewers et al. |
| 7,749,250 | B2 | 7/2010 | Stone et al. |
| 7,758,594 | B2 | 7/2010 | Lamson et al. |
| 7,776,041 | B2 | 8/2010 | Walters |
| 7,819,895 | B2 | 10/2010 | Ginn et al. |
| 7,857,830 | B2 | 12/2010 | Stone et al. |
| 7,875,058 | B2 | 1/2011 | Holmes, Jr. |
| 7,905,903 | B2 | 3/2011 | Stone et al. |
| 7,905,904 | B2 | 3/2011 | Stone et al. |
| 7,909,851 | B2 | 3/2011 | Stone et al. |
| 7,938,847 | B2 | 5/2011 | Fanton et al. |
| 7,959,650 | B2 | 6/2011 | Kaiser et al. |
| 7,981,140 | B2 | 7/2011 | Burkhart |
| 7,998,203 | B2 | 8/2011 | Blum |
| 8,062,334 | B2 | 11/2011 | Green et al. |
| 8,075,574 | B2 | 12/2011 | May et al. |
| 8,088,130 | B2 | 1/2012 | Kaiser et al. |
| 8,114,127 | B2 | 2/2012 | West, Jr. |
| 8,114,128 | B2 | 2/2012 | Cauldwell et al. |
| 8,118,836 | B2 | 2/2012 | Denham et al. |
| 8,128,658 | B2 | 3/2012 | Kaiser et al. |
| 8,137,382 | B2 | 3/2012 | Denham et al. |
| 8,167,906 | B2 | 5/2012 | Cauldwell et al. |
| 8,221,454 | B2 | 7/2012 | Schaffhausen |
| 8,231,654 | B2 | 7/2012 | Kaiser et al. |
| 8,251,998 | B2 | 8/2012 | Hoeppner et al. |
| 2001/0010005 | A1 | 7/2001 | Kammerer et al. |
| 2001/0014825 | A1 | 8/2001 | Burke et al. |
| 2001/0019649 | A1 | 9/2001 | Field et al. |
| 2001/0037131 | A1 | 11/2001 | Schmieding et al. |
| 2001/0037153 | A1 | 11/2001 | Rockwood et al. |
| 2001/0041916 | A1 | 11/2001 | Bonutti |
| 2001/0041937 | A1 | 11/2001 | Rieser et al. |
| 2001/0041938 | A1 | 11/2001 | Hein |
| 2001/0044639 | A1 | 11/2001 | Levinson |

| | | |
|---|---|---|
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |

| | | |
|---|---|---|
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122611 A1 | 6/2006 | Morales et al. |
| 2006/0135958 A1 | 6/2006 | Marissen et al. |
| 2006/0149266 A1 | 7/2006 | Cordasco |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0229671 A1 | 10/2006 | Steiner et al. |
| 2006/0235407 A1 | 10/2006 | Wang et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0280768 A1 | 12/2006 | Hwang et al. |
| 2006/0282082 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0219558 A1 | 9/2007 | Deutsch |
| 2007/0225719 A1 | 9/2007 | Stone et al. |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0276387 A1 | 11/2007 | Morales et al. |
| 2008/0027446 A1 | 1/2008 | Stone et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0161852 A1 | 7/2008 | Kaiser et al. |
| 2008/0161861 A1 | 7/2008 | Huebner |
| 2008/0172097 A1 | 7/2008 | Lerch et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0248091 A1 | 10/2009 | Teague et al. |
| 2009/0265014 A1 | 10/2009 | May et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |

| | | | | | | |
|---|---|---|---|---|---|---|
| 2010/0256677 A1 | 10/2010 | Albertorio et al. | | EP | 0497079 | 8/1992 |
| 2010/0268273 A1 | 10/2010 | Albertorio et al. | | EP | 0502509 | 9/1992 |
| 2010/0268275 A1 | 10/2010 | Stone et al. | | EP | 0502698 | 9/1992 |
| 2010/0270306 A1 | 10/2010 | Shiffer | | EP | 520177 | 12/1992 |
| 2010/0292792 A1 | 11/2010 | Stone et al. | | EP | 0546726 | 6/1993 |
| 2010/0305698 A1 | 12/2010 | Metzger et al. | | EP | 0574707 | 12/1993 |
| 2010/0305709 A1 | 12/2010 | Metzger et al. | | EP | 0582514 | 2/1994 |
| 2010/0312341 A1 | 12/2010 | Kaiser et al. | | EP | 0591991 | 4/1994 |
| 2011/0009885 A1 | 1/2011 | Graf et al. | | EP | 0598219 | 5/1994 |
| 2011/0087284 A1 | 4/2011 | Stone et al. | | EP | 0611551 A1 | 8/1994 |
| 2011/0098727 A1 | 4/2011 | Kaiser et al. | | EP | 0627203 | 12/1994 |
| 2011/0106153 A1 | 5/2011 | Stone et al. | | EP | 0651979 | 5/1995 |
| 2011/0160767 A1 | 6/2011 | Stone et al. | | EP | 0669110 | 8/1995 |
| 2011/0160768 A1 | 6/2011 | Stone et al. | | EP | 0686373 | 12/1995 |
| 2011/0208239 A1 | 8/2011 | Stone et al. | | EP | 0702933 | 3/1996 |
| 2011/0208240 A1 | 8/2011 | Stone et al. | | EP | 0775473 | 5/1997 |
| 2011/0213416 A1 | 9/2011 | Kaiser | | EP | 0913123 | 5/1999 |
| 2011/0218625 A1 | 9/2011 | Berelsman et al. | | EP | 0913131 | 5/1999 |
| 2011/0224799 A1 | 9/2011 | Stone | | EP | 99121106 | 10/1999 |
| 2011/0264141 A1 | 10/2011 | Denham et al. | | EP | 991210527 | 10/1999 |
| 2011/0270278 A1 | 11/2011 | Overes et al. | | EP | 0995409 | 4/2000 |
| 2011/0270306 A1 | 11/2011 | Denham et al. | | EP | 1013229 | 6/2000 |
| 2012/0041485 A1 | 2/2012 | Kaiser et al. | | EP | 1093773 | 4/2001 |
| 2012/0041486 A1 | 2/2012 | Stone et al. | | EP | 1093774 | 4/2001 |
| 2012/0046693 A1 | 2/2012 | Denham et al. | | EP | 1555945 | 7/2005 |
| 2012/0053630 A1 | 3/2012 | Denham et al. | | FR | 2622790 | 5/1989 |
| 2012/0059417 A1 | 3/2012 | Norton et al. | | FR | 2655840 | 6/1991 |
| 2012/0059418 A1 | 3/2012 | Denham et al. | | FR | 2682867 | 4/1993 |
| 2012/0095470 A1 | 4/2012 | Kaiser et al. | | FR | 2687911 | 9/1993 |
| 2012/0123474 A1 | 5/2012 | Zajac et al. | | FR | 2688689 | 9/1993 |
| 2012/0123541 A1 | 5/2012 | Albertorio et al. | | FR | 2704140 | 10/1994 |
| 2012/0150297 A1 | 6/2012 | Denham et al. | | FR | 2717070 | 9/1995 |
| 2012/0165866 A1 | 6/2012 | Kaiser et al. | | FR | 2723528 | 2/1996 |
| 2012/0165867 A1 | 6/2012 | Denham et al. | | FR | 2744010 | 8/1997 |
| 2012/0165938 A1 | 6/2012 | Denham et al. | | FR | 2745999 | 9/1997 |
| 2012/0197271 A1 | 8/2012 | Astorino et al. | | FR | 2770764 | 5/1999 |
| | | | | GB | 401677 | 11/1933 |
| FOREIGN PATENT DOCUMENTS | | | | GB | 1413477 | 11/1975 |
| AU | 5850469 | 1/1971 | | GB | 1485681 | 9/1977 |
| AU | 5963869 | 2/1971 | | GB | 2083751 | 3/1982 |
| AU | 1505470 | 11/1971 | | GB | 2118474 | 11/1983 |
| AU | 2223767 | 5/1973 | | GB | 2227175 | 7/1990 |
| AU | 3615171 | 5/1973 | | GB | 2253147 A | 9/1992 |
| AU | 5028569 | 9/1973 | | GB | 2312376 | 10/1997 |
| AU | 7110887 | 10/1987 | | GB | 2403416 A | 1/2005 |
| AU | 639410 | 11/1989 | | JP | 5362911 | 5/1978 |
| AU | 651929 | 8/1994 | | JP | 5362912 | 5/1978 |
| DE | 2529669 | 3/1976 | | JP | 5374942 | 6/1978 |
| DE | 2747312 | 4/1979 | | JP | 5378230 | 6/1978 |
| DE | 2818254 | 10/1979 | | JP | 62159647 | 7/1987 |
| DE | 2919009 | 11/1979 | | JP | 62295657 | 12/1987 |
| DE | 3027138 | 12/1981 | | JP | 5269160 | 10/1993 |
| DE | 3225620 | 2/1983 | | JP | 5300917 | 11/1993 |
| DE | 3136083 | 3/1983 | | JP | 751292 | 2/1995 |
| DE | 233303 | 2/1986 | | JP | 10211213 | 8/1998 |
| DE | 4127550 | 2/1993 | | WO | WO-8300615 | 3/1983 |
| DE | 4302397 | 7/1993 | | WO | WO-8603666 | 7/1986 |
| DE | 29621340 | 5/1998 | | WO | WO-8701270 | 3/1987 |
| DE | 19841252 | 3/2000 | | WO | WO-8901767 | 3/1989 |
| EP | 0108912 | 5/1984 | | WO | WO-8909030 | 10/1989 |
| EP | 0129442 | 12/1984 | | WO | WO-8910096 | 11/1989 |
| EP | 0172130 | 2/1986 | | WO | WO-9008510 | 8/1990 |
| EP | 0241240 | 10/1987 | | WO | WO-9203980 | 3/1992 |
| EP | 0241792 | 10/1987 | | WO | WO-9314705 | 8/1993 |
| EP | 0260970 | 3/1988 | | WO | WO-9315694 | 8/1993 |
| EP | 0270704 | 6/1988 | | WO | WO-9502373 | 1/1995 |
| EP | 0282789 | 9/1988 | | WO | WO-9503003 | 2/1995 |
| EP | 0315371 | 5/1989 | | WO | WO-9529637 | 11/1995 |
| EP | 0317406 | 5/1989 | | WO | WO-9532670 | 12/1995 |
| EP | 0340159 | 11/1989 | | WO | WO-9629029 | 9/1996 |
| EP | 0346183 | 12/1989 | | WO | WO-9737603 | 10/1997 |
| EP | 0349173 | 1/1990 | | WO | WO-9812991 | 4/1998 |
| EP | 0374088 | 6/1990 | | WO | WO-9812992 | 4/1998 |
| EP | 0409364 | 1/1991 | | WO | WO-9822047 | 5/1998 |
| EP | 0415915 | 3/1991 | | WO | WO-9822048 | 5/1998 |
| EP | 0440991 | 8/1991 | | WO | WO-9901084 | 1/1999 |
| EP | 0441065 | 8/1991 | | WO | WO-9912480 | 3/1999 |
| EP | 0451932 | 10/1991 | | WO | WO-9944544 | 9/1999 |
| EP | 0464480 | 1/1992 | | WO | WO-0040159 | 7/2000 |

| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2004091412 A1 | 10/2004 |
| WO | WO-2005104992 A1 | 11/2005 |
| WO | WO-2008002550 A2 | 1/2008 |
| WO | WO-2009012021 A1 | 1/2009 |
| WO | WO-2011112371 A1 | 9/2011 |
| WO | WO-2011150238 A1 | 12/2011 |

OTHER PUBLICATIONS

"Arthroscopic Meniscal Repair using the Meniscal Cinch™", Surgical Technique brochure. (2008) Arthrex® 6 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 paages) Ortheon® Medical.
"EZ Loc Femoral Fixation Device," copyright 2005 Arthrotek, Inc. (8 sheets).
"Juggerknot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"Panalok Anchor with PDS II and Ethibond Suture", Mitek Products Ethicon, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Interview Summary mailed Jul. 14, 2011 for U.S. Appl. No. 12/196,407.
Interview Summary mailed Jul. 14, 2011 for U.S. Appl. No. 12/196,410, filed Aug. 22, 2008.
Interview Summary mailed Jun. 20, 2011 for U.S. Appl. No. 12/196,405.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Notice of Allowance (Supplemental Notice of Allowability) mailed Apr. 15, 2011 for U.S. Appl. No. 12/196,398, filed Aug. 22, 2008; now U.S. Patent No. 7,959,650.
Notice of Allowance (Supplemental Notice of Allowability) mailed Mar. 9, 2011 for U.S. Appl. No. 12/196,398, filed Aug. 22, 2008; now U.S. Patent No. 7,959,650.
Notice of Allowance mailed Jun. 1, 2009 for U.S. Appl. No. 11/541,506, filed Sep. 29, 2006; now U.S. Patent No. 7,601,165.
Notice of Allowance with Interview Summary mailed Aug. 31, 2011 for U.S. Appl. No. 12/474,802, filed Nov. 3, 2010.
Notice of Allowance with Interview Summary mailed Feb. 3, 2011 for U.S. Appl. No. 12/196,398 filed Aug. 22, 2010; now U.S. Patent No. 7,959,650.
Office Action mailed Apr. 11, 2011 for U.S. Appl. No. 12/196,405.
Office Action mailed May 19, 2009 for U.S. Appl. No. 11/541,505, filed Sep. 29, 2006; now U.S. Patent No. 7,658,751.
Office Action mailed May 4, 2011 for U.S. Appl. No. 12/196,407, filed Aug. 22, 2008.
Office Action mailed May 9, 2011 for U.S. Appl. No. 12/196,410, filed Aug. 22, 2008.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Restriction Requirement mailed Mar. 22, 2011 for U.S. Appl. No. 12/196,407, filed Aug. 22, 2008.
Restriction Requirement mailed Mar. 9, 2009 for U.S. Appl. No. 11/541,505, filed Sep. 29, 2006; now U.S. Patent No. 7,658,751.
Restriction Requirement mailed Mar. 9, 2009 for U.S. Appl. No. 11/541,506, filed Sep. 29, 2006; now U.S. Patent No. 7,601,165.
Restriction Requirement mailed Sep. 29, 2010 for U.S. Appl. No. 12/196,398, filed Aug. 22, 2008; now U.S. Patent No. 7,959,650.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
Invitation to Pay Additional Fees mailed Jul. 19, 2012, for PCT/US2012/037703 claiming benefit of U.S. Appl. No. 13/109,667, filed May 7, 2011.
US 6,238,418, 05/2001, Schwartz et al. (withdrawn)

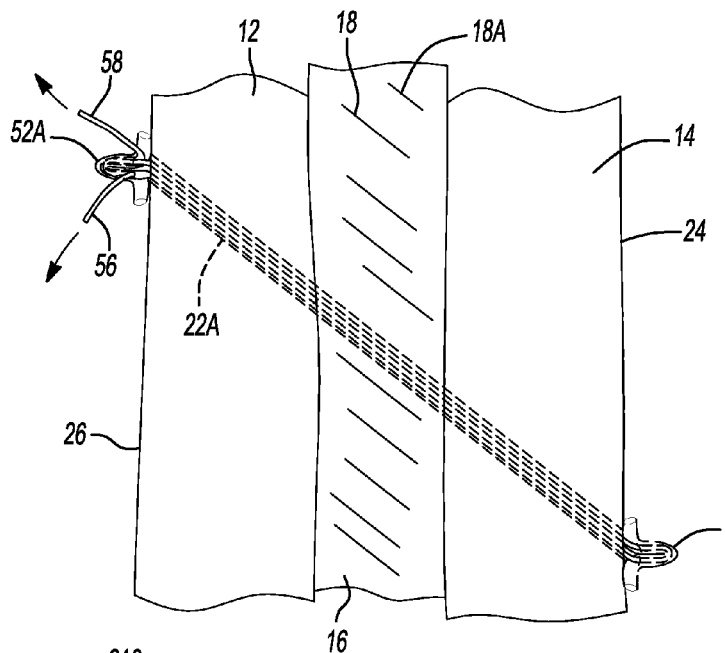
*Fig-11*
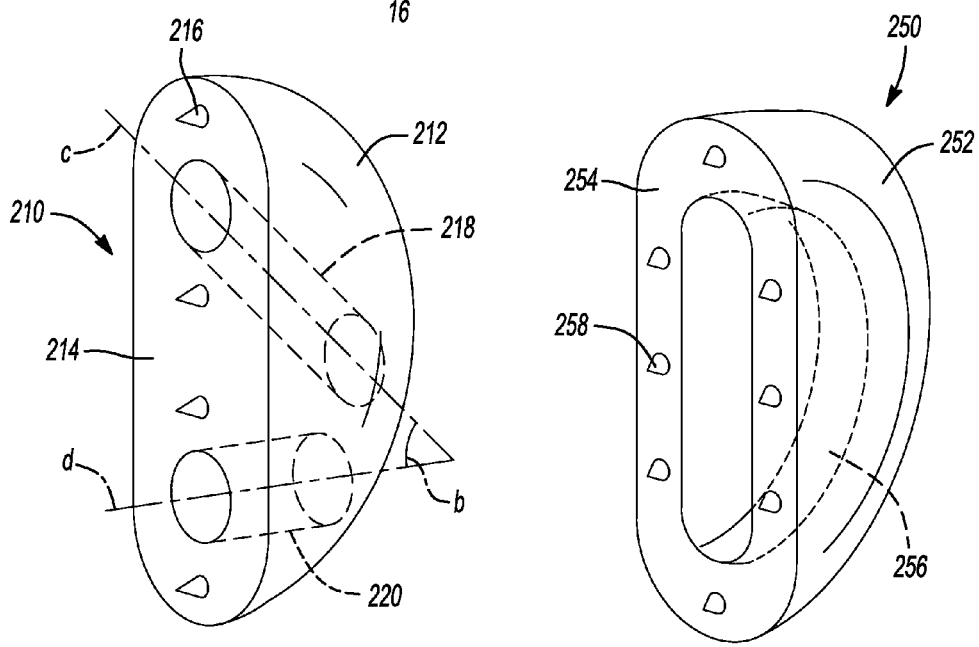
*Fig-12*  *Fig-13*

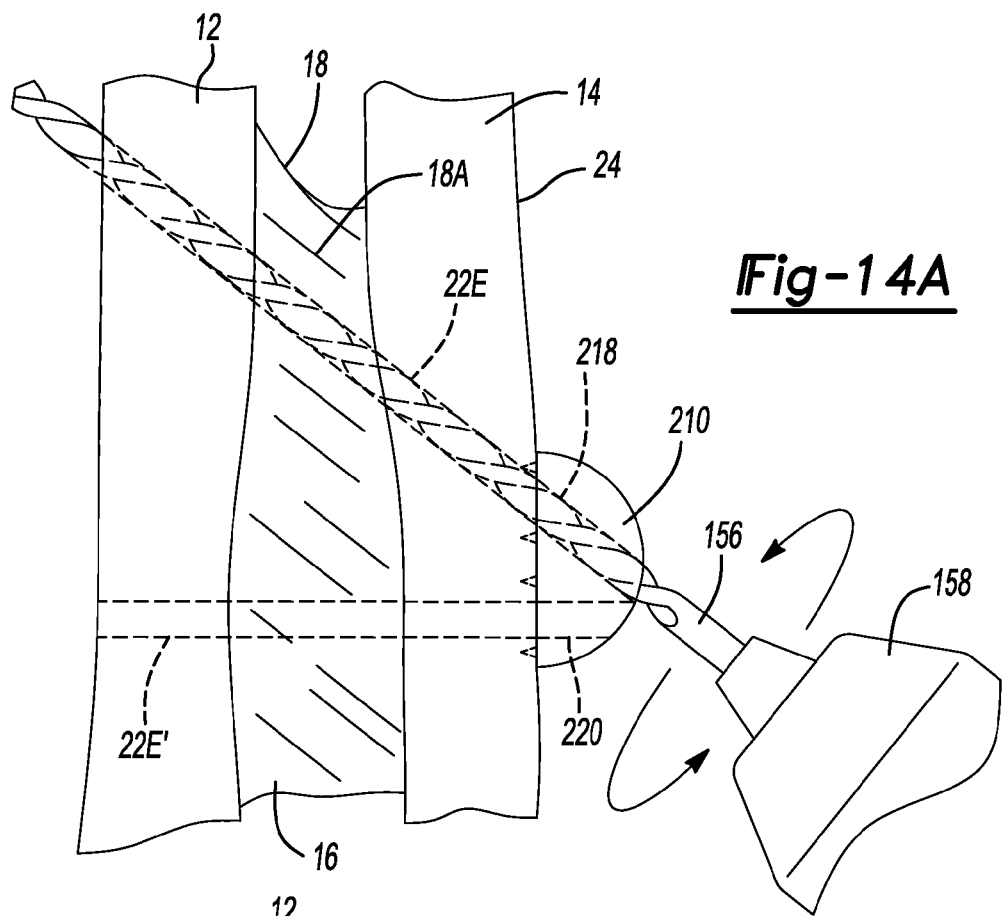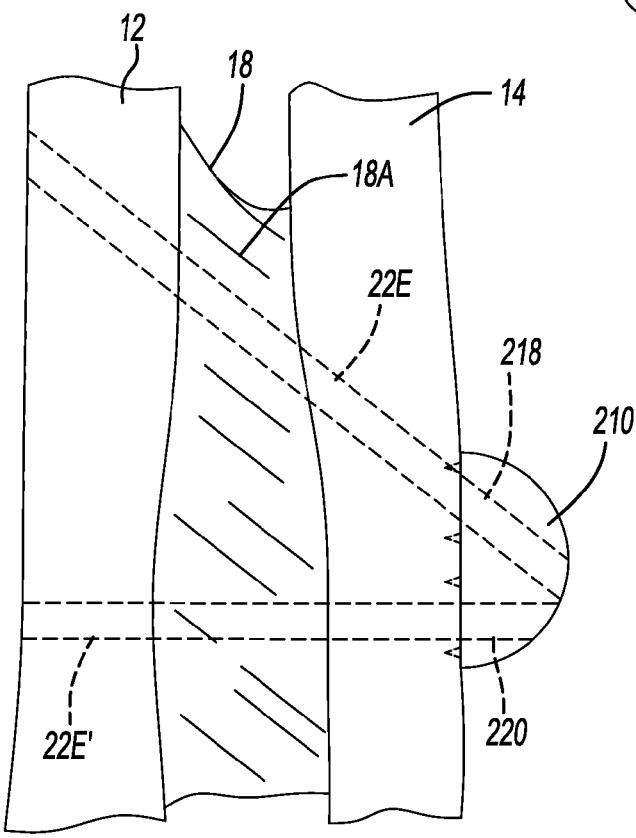

METHOD AND APPARATUS FOR INTEROSSEOUS MEMBRANE RECONSTRUCTION

CROSS-REFERENCE TO RELATED APPLICATIONS

The present application is related to U.S. patent application Ser. No. 13/281,009 entitled "Method and Apparatus for Fracture Fixation" filed concurrently herewith. Each of these disclosures are incorporated by reference.

FIELD

The present disclosure relates to methods and devices for interosseous membrane reconstruction.

BACKGROUND

This section provides background information related to the present disclosure which is not necessarily prior art.

The interosseous membrane is a broad and thin plane of fibrous connective tissue that separates various different bones of the human body. For example, the long bones of the lower arm and the leg are connected by interosseous membranes. In the arm, an interosseous membrane extends between the radius and ulna to transfer forces from the radius to the ulna and humerus. As the forearm moves from pronation to supination, the interosseous membrane fibers move from a relaxed state to a tense neutral position, and then return to the relaxed state as the forearm enters supination. In the leg, the interosseous membrane extends between the tibia the fibula, running along the crest of each bone. It fulfills many of the same functions in the leg as in the arm.

Tears in the membrane can occur as a result of severe trauma or fracturing of adjacent bone, and may also be created during surgery. To facilitate healing of such tears, pins are often inserted through the bones surrounding the interosseous membrane, such as the radius and the ulna. Use of pins, however, can hinder range of motion, such as pronation and supination of the forearm for example.

SUMMARY

This section provides a general summary of the disclosure, and is not a comprehensive disclosure of its full scope or all of its features.

The present teachings provide for a method for repairing a defect in an interosseous membrane located between a first bone and a second bone. The method includes: coupling a flexible member to the first bone and the second bone, the flexible member extending past a first area of the interosseous membrane between the first bone and the second bone; and orienting the flexible member such that the flexible member extends generally parallel to fibers of the first area of the interosseous membrane.

The present teachings further provide for a method for repairing a defect in an interosseous membrane located between a first bone and a second bone. The method includes: orienting a first suture portion such that the first suture portion extends generally parallel to fibers of a first area of the interosseous membrane; coupling the first suture portion to the first bone and the second bone, the first suture portion extending past a first area of the interosseous membrane between the first bone and the second bone; orienting and coupling a second suture portion to the first bone and the second bone, the second suture portion extending past the first area of the interosseous membrane between the first bone and the second bone.

The present teachings also provide for a kit for repairing a defect in an interosseous membrane located between a first bone and a second bone, the kit includes at least one suture and a first drill guide. The first drill guide includes a body; a bone engagement surface; a first through hole extending through the body, the first through hole defines a first longitudinal axis; and a second through hole extending through the body, the second through hole defines a second longitudinal axis that is angled one of about 20° to about 25° or about 40° to about 45° relative to the first longitudinal axis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 11 illustrates the suture of FIG. 2 secured to the forearm according to the present teachings;

FIG. 12 is a perspective view of a drill guide according to the present teachings;

FIG. 13 is a perspective view of pin guide according to the present teachings;

FIG. 14A illustrates the drill guide of FIG. 12 mounted to the forearm to guide a drill to form a first bore and a second bore in the forearm;

FIG. 14B illustrates first and second bores formed the forearm, the bores having been formed with the drill guided by the drill guide;

Corresponding reference numerals indicate corresponding parts throughout the several views of the drawings.

DETAILED DESCRIPTION

Example embodiments will now be described more fully with reference to the accompanying drawings.

Figure 1A:
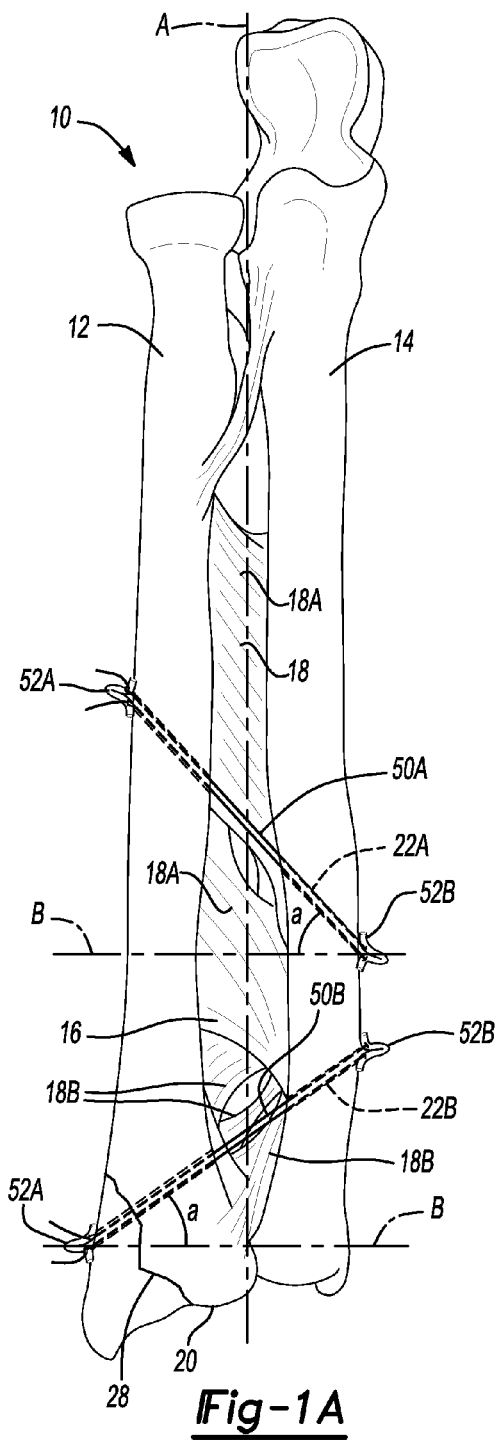
FIG. 1A is an anterior view of a forearm with sutures extending between a radius and ulna of the forearm in accordance with the present teachings.
Figure 1B:
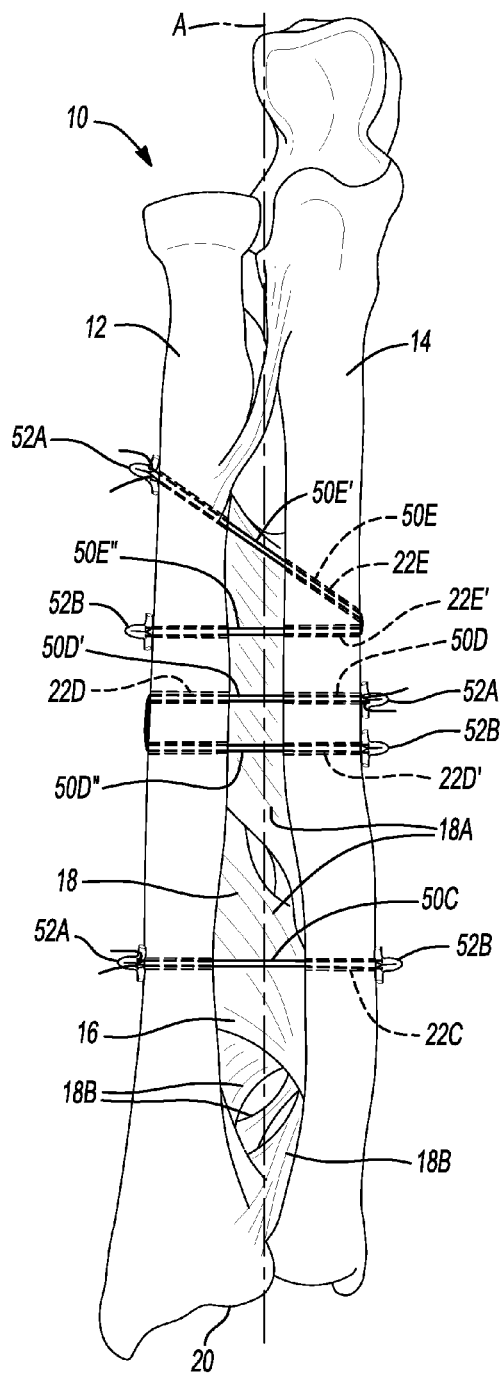
FIG. 1B is an anterior view of additional sutures extending between the radius and the ulna.

FIGS. 1A and 1B illustrate an anterior view of a forearm 10 including a radius 12, an ulna 14, and an interosseous membrane 16 extending between the radius 12 and the ulna 14 and across a longitudinal axis A of the forearm 10. The interosseous membrane 16, for example, connects the radius 12 to the ulna 14, facilitates movement of the forearm 10 from pronation to supination, and transfers forces between the radius 12, the ulna 14, and the humerus (not illustrated). The interosseous membrane 16 includes tissue having a plurality of fibers 18.

A first group of fibers 18A generally extend obliquely across the longitudinal axis A from the radius 12 proximally to the ulna 14 distally. A second group of fibers 18B extend obliquely across the longitudinal axis A from the radius 12 distally to the ulna 14 proximally. The second group of fibers 18B is generally smaller than the first group of fibers 18A and is located between the first group of fibers 18A and a distal end 20 of the forearm 10. One skilled in the art will recognize the various orientations of the fibers 18 and the angle of the fibers 18 with respect to the radius 12 and the ulna 14. One skilled in the art will also recognize that no two interosseous membranes are exactly the same, but that the fibers 18 among different patients are similarly orientated, as generally illustrated in FIGS. 1A and 1B, and as described above.

The radius 12 and the ulna 14 can be further connected by a plurality of flexible members, such as sutures 50, which extend through each of the radius 12, the interosseous membrane 16, and the ulna 14. As further described herein, the sutures 50 can be any suitable suture and can be anchored to the radius 12 and the ulna 14 in any suitable manner, such as with a first anchor 52A at the radius 12 and a second anchor 52B at the ulna 14. The sutures 50 supplement the connection between the radius 12 and the ulna 14 provided by the interosseous membrane 16, such as in instances where the interosseous membrane 16 has been damaged due to trauma or during surgery. This damage can include tears in the interosseous membrane 16 or separation of the interosseous membrane from either the radius 12 or the ulna 14.

The sutures 50 each generally extend through a bore 22 formed through the radius 12, the ulna 14, and the interosseous membrane 16. Each of the sutures 50 are generally positioned and orientated to permit natural movement of the radius 12, the ulna 14, and the interosseous membrane 16. For example and with reference to FIG. 1A, suture 50A is orientated such that it extends generally parallel to the interosseous fibers 18 of the first group of interosseous fibers 18A and across the first group of interosseous fibers 18A between the radius 12 and the ulna 14; and suture 50B is orientated such that it extends generally parallel to the interosseous fibers 18 of the second group of interosseous fibers 18B and across the second group of interosseous fibers 18B between the radius 12 and the ulna 14. The suture 50A and the suture 50B are thus each generally orientated at an angle "a" of from about 5° to about 55°, such as about 20° to about 25° or about 40° to about 45°, relative to a line B extending perpendicular to the longitudinal axis A.

The suture 50A is seated in a first bore 22A and the suture 50B is seated in a second bore 22B. Orienting the sutures 50A and 50B parallel to fibers 18 of the first and the second groups of interosseous fibers 18A and 18B respectively generally permits natural movement of the interosseous membrane 16, such as between pronation and supination of the forearm 10, and allows natural loading between the radius 12 and the ulna 14. Such natural movement and loading is not permitted, but is rather restricted by, use of rigid fixation members, such as rigid pins. To stabilize a bone fracture, such as a fracture 28 of the radius 12, the suture 50B can be orientated such that it extends through the fracture 28.

With additional reference to FIG. 1B, the sutures 50 can be provided at a variety of other orientations as well, in addition to or in place of the orientations of sutures 50A and 50B of FIG. 1A. For example, one or more of the sutures 50 can be orientated so as to extend across the interosseous membrane 16 substantially perpendicular to the longitudinal axis A, such as suture 50C seated in bore 22C. Orienting the suture 50C perpendicular to the longitudinal axis A stabilizes relative movement of the radius 12 and the ulna 14 perpendicular to the longitudinal axis A. In other words, the radius 12 and the ulna 14 are stabilized so that they do not move relative to each other perpendicular to the longitudinal axis A. The suture 50C is anchored at the radius 12 with the first anchor 52A and at the ulna 14 with the second anchor 52B.

Any of the sutures 50 can be implanted such that they loop through the forearm 10 and are anchored to only one of either the radius 12 or the ulna 14. For example, both the first anchor 52A and the second anchor 52B of the suture 50D are mounted to the ulna 14. A first portion 50D' of the suture 50D extends from the first anchor 52A to the radius 12 through a first bore 22D. Upon exiting the first bore 22D at the radius 12, the suture 50D loops back into the radius 12 such that a second portion 50D" extends through the radius 12 to the ulna 14 through a second bore 22D', where the suture 50D is secured by the second anchor 52B. Each of the first bore 22D and the second bore 22D' are extended substantially perpendicular to the longitudinal axis A, and thus the first and second portions 50D' and 50D" of the suture 50D are perpendicular to the longitudinal axis A as well. While the suture 50D is secured to the ulna 14 with the first anchor 52A and the second anchor 52B, the suture 50D can be reversed such that the first anchor 52A and the second anchor 52B are secured to the radius 12. By looping the suture 50D through the forearm 10 as illustrated, the suture 50D can provide additional stability to the radius 12 and the ulna 14 perpendicular to the longitudinal axis A.

As illustrated in FIG. 1B, suture 50E provides another possible orientation for the suture 50. The suture 50E is orientated such that the first anchor 52A and the second anchor 52B are both anchored to the radius 12. A first portion 50E' of the suture 50E extends from the first anchor 52A to the ulna 14 through a first bore 22E. Upon exiting the first bore 22E at the ulna 14, the suture 50E loops back into the ulna 14 such that a second portion 50E" extends through the ulna 14 to the radius 12 through a second bore 22E', where the suture 50E is secured by the second anchor 52B. The first bore 22E is angled such that it extends through the interosseous membrane 16 substantially parallel to the fibers 18 of the first group of interosseous fibers 18A. Thus, the first portion 50E' is also substantially parallel to the fibers 18 of the first group of interosseous fibers 18A. The second bore 22E' is substantially perpendicular to the longitudinal axis A, and thus the second portion 50E" of the suture 50E is perpendicular to the longitudinal axis A. The first portion 50E' is angled about 5° to about 55° relative to the second portion 50E", such as about 20° to about 25° or about 40° to about 45°.

Orienting the second portion 50E" generally perpendicular to the longitudinal axis A stabilizes the radius 12 with respect to the ulna 14 perpendicular to the longitudinal axis A and orienting the first portion 50E' generally parallel to the fibers 18 of the first group of interosseous fibers 18A generally permits natural movement of the radius 12 with respect to the ulna 14, such as during supination and pronation of the forearm 10, and distributes load between the radius 12 and the ulna 14 similar as to how the load would be distributed naturally. Thus, the suture 50E is a dual purpose suture that generally provides two stabilizing effects. First, the first portion 50E' permits load transfer between the radius 12 and the ulna 14 in a manner similar to that which occurs naturally. The second portion 50E" stabilizes the radius 12 and the ulna 14 along the longitudinal axis A so that the radius 12 and the ulna 14 do not move relative to each other perpendicular to the longitudinal axis A.

The forearm 10 can be provided with any combination of the sutures 50A-50E, and is thus not limited to the arrangements illustrated in FIGS. 1A and 1B. For example, each one of the sutures 50A-50E can be included in a single forearm 10. The arrangement of the sutures 50A-50E can be determined by a physician based on, for example, the patient's anatomy, damage to the interosseous membrane 16, and observed orientations of the patient's interosseous fibers 18.

Figure 2:
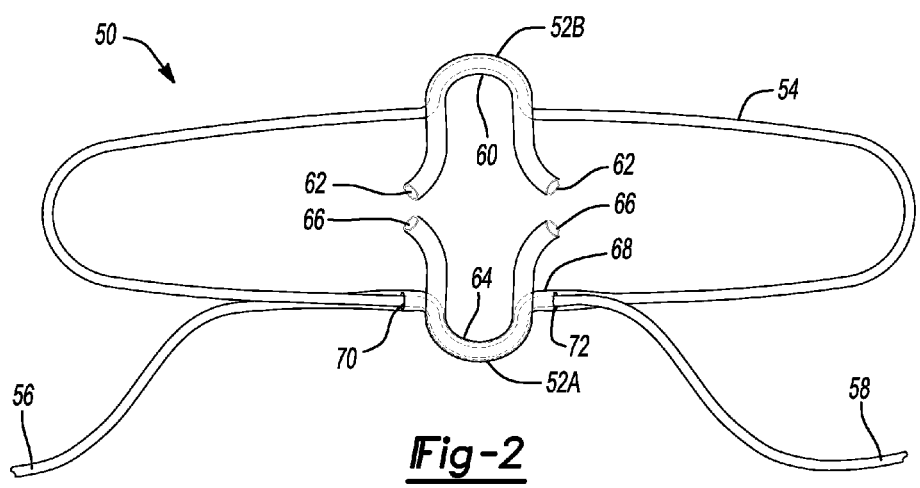
FIG. 2 illustrates an exemplary suture according to the present teachings.

With additional reference to FIG. 2, further details of the suture 50, which generally includes a suture construct or assembly, will be described. The description of the suture 50 generally applies to each of the sutures 50A-50E described above. The suture 50 can generally include a hollow braided suture strand 54 including a first end 56 and a second end 58. The second anchor 52B is approximately equidistant between the first end 56 and the second end 58. The second anchor 52B is generally U-shaped and flexible. The second anchor 52B includes a base 60 and a pair of feet 62, which extend from the base 60. The base 60 is connected to the suture strand 54 in any suitable manner, and may be integral with the suture strand 54 as illustrated.

The first anchor 52A is between the first end 56 of the suture strand 54 and the second anchor 52B. The first anchor 52A includes a base 64 and a pair of feet 66. Integral with the base 64 and the suture strand 54 is a sleeve portion 68 of the suture 54 that includes a first opening 70 and a second opening 72 between braided fibers that is opposite to the first opening 70. The second end 58 of the suture strand 54 is inserted through the sleeve 68 such that the suture strand 54 enters the sleeve 68 through the first opening 70 and exits the sleeve 68 through the second opening 72.

The suture 50 is a knotless, self-locking suture. As the first and second ends 56 and 58 are pulled, friction between the interior of the sleeve 68 and the portion of the suture strand 54 located within the sleeve 68 causes the suture 50 to "automatically" lock in a reduced size or diameter configuration in which tension is maintained without use of a knot. The suture 50 is similar to the self-locking suture construct 300A of FIG. 15 of U.S. application Ser. No. 12/915,962 filed on Oct. 29, 2010, titled Method and Apparatus for Securing Soft Tissue to Bone, and assigned to Biomet Sports Medicine, LLC, the disclosure of which is incorporated herein by reference. Additional description of the suture 50 is thus included in U.S. application Ser. No. 12/915,962. Additional sutures that can be used in accordance with the present teachings include those disclosed in U.S. Pat. No. 7,658,751, which issued on Feb. 9, 2010 and is assigned to Biomet Sports Medicine, LLC, Warsaw, Ind. The disclosure of U.S. Pat. No. 7,658,751 is incorporated herein by reference.

Figure 3:
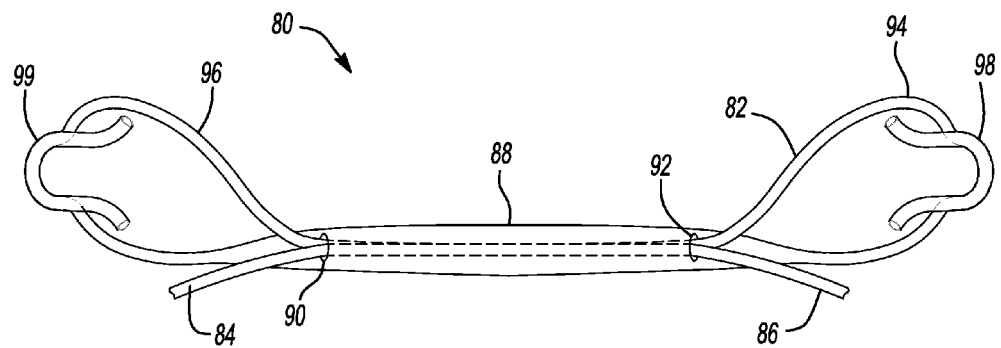
FIG. 3 illustrates another suture according to the present teachings.

The suture 50 can be replaced with any suitable biocompatible fastening device that will permit natural movement of the interosseous membrane 16. For example and with reference to FIG. 3, a suture 80 can be used. The suture 80 is a self-locking suture that includes a hollow, braided suture strand 82 with a first end 84 and a second end 86. A sleeve portion 88 of the suture 80 is located about halfway between the first end 84 and the second end 86. The sleeve 88 includes a first opening 90 and a second opening 92 between braided fibers. The first end 84 is inserted into the sleeve 88 through the second opening 92 and passed through the sleeve 88 such that the first end 84 extends out through the first opening 90 of the sleeve 88. The second end 86 is inserted into the sleeve 88 through the first opening 90 and passed through the sleeve 88 such that the second end 86 extends out through the second opening 92 of the sleeve 88. Inserting the first and the second ends 84 and 86 through the sleeve 88 causes the suture strand 82 to form a first loop 94 including a first anchor 98 and a second loop 96 including a second anchor 99. As the first end 84 and the second end 86 are pulled through the sleeve 88, friction in the sleeve 88 causes the suture 80 to "automatically" lock in a reduced size or diameter configuration in which tension is maintained without use of a knot. The suture 80 is similar to the self-locking suture construct 250 of FIG. 13 of U.S. application Ser. No. 12/915,962, the disclosure of which has been incorporated herein by reference. Additional description of the suture 80 is thus included in U.S. application Ser. No. 12/915,962.

In addition to the sutures and suture constructs described herein and incorporated herein by reference, any other suitable suture, suture construct, knit, or flexible member, such as a Nitinol strand, can be inserted in the bores 22 to connect the radius 12 and ulna 14 in a manner that will transfer loads between the radius 12 and ulna 14, provide at least near natural range of motion between the radius 12 and ulna 14, and stabilize the radius 12 and ulna 14 along the longitudinal axis A such that neither the radius 12 nor the ulna 14 move relative to each other perpendicular to the longitudinal axis A.

Figure 4:
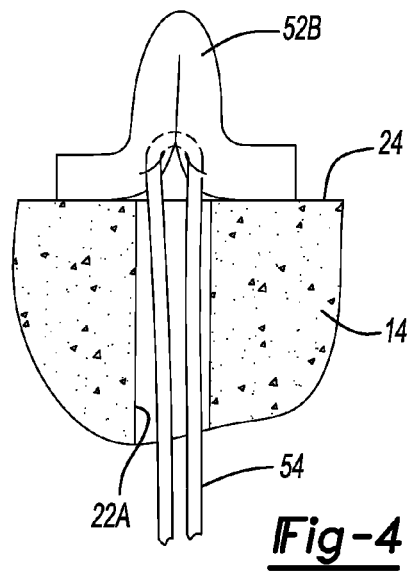
FIG. 4 illustrates an end of the suture of FIG. 2 anchored at an exterior of a bone of the forearm.

The anchors 52A, 52B, 98, and 99 are all configured to expand when compressed against bone so as to anchor to an exterior of the bone. For example and with reference to FIG. 4, as the suture strand 54 is pulled away from an outer surface 24 of the ulna 14 through the first bore 22A, the second anchor 52B compresses against the outer surface 24 and expands to anchor the suture 50 to the ulna 14.

Figure 5:
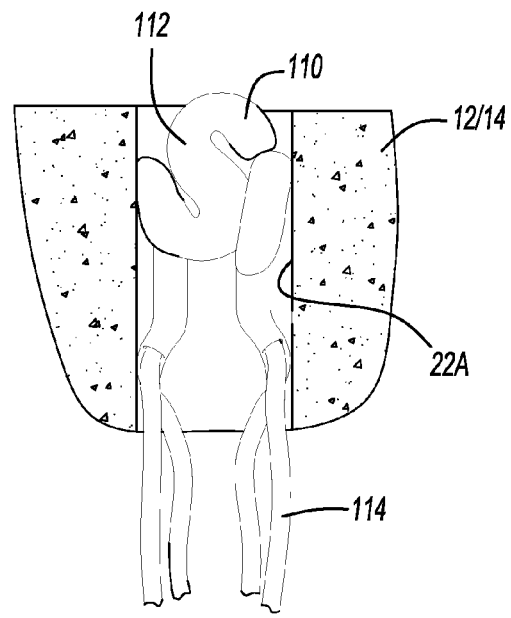
FIG. 5 illustrates another suture according to the present teachings, the suture anchored at an interior of a bone of the forearm.

With additional reference to FIG. 5, any one or more of the sutures 50 can be anchored at an interior of the radius 12 or the ulna 14 with an anchor 110. The anchor 110, which can be similar to the anchor 52 but collapsed to fit within the first bore 22A, expands to form an anchoring mass 112 upon tightening of suture strands 114 to thereby secure the anchor 110 to the radius 12 or ulna 14. The anchor 110 is similar to the anchor 150 of the suture construct 184 disclosed in U.S. application Ser. No. 12/915,962, the disclosure of which has been incorporated herein by reference. Additional description of the anchor 150 is thus included in U.S. application Ser. No. 12/915,962.

Figure 6:
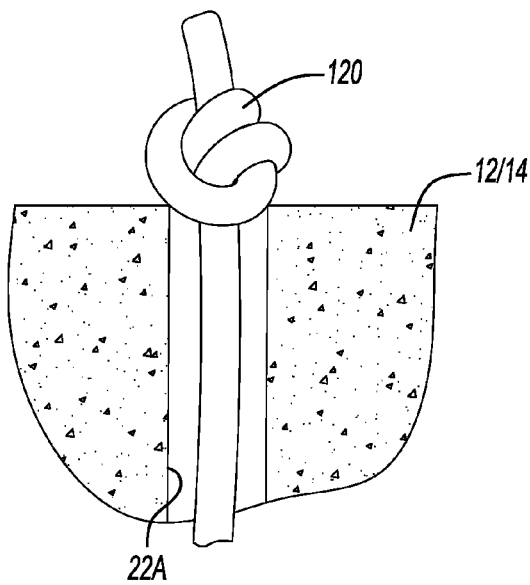
FIG. 6 illustrates an additional suture according to the present teachings, the suture anchored at an exterior of a bone of the forearm.

With reference to FIG. 6, any of the sutures 50, any of the other sutures described herein, and any of the sutures incorporated by reference can be secured to the radius 12 or the ulna 14 with a knot 120 having an outer diameter larger than the bore that the suture is seated within, such as the first bore 22A.

Figure 7:
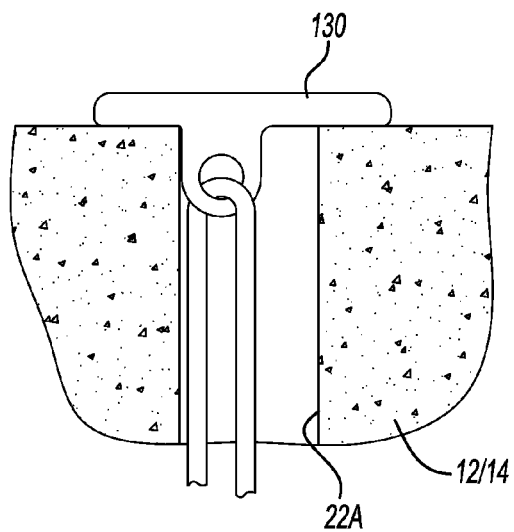
FIG. 7 illustrates yet another suture according to the present teachings, the suture anchored to an exterior of a bone of the forearm.

With reference to FIG. 7, any of the sutures 50, any of the other sutures described herein, and any of the sutures incorporated by reference can be secured to the radius 12 or the ulna 14 with a lever anchor 130 movable between a non-active position and an active position. In the non-active position, the lever anchor 130 is orientated such that is can pass through the bore that the suture is seated within, such as the first bore 22A. In the activated position, illustrated in FIG. 7, the lever anchor 130 extends across the bore at an exterior of the radius 12 or ulna 14 to secure the anchor 130 to the radius 12 or ulna 14. As an alternative to the illustrated anchor 130, any other suitable anchor member or button can be mounted to suture strands 14.

Figure 8:
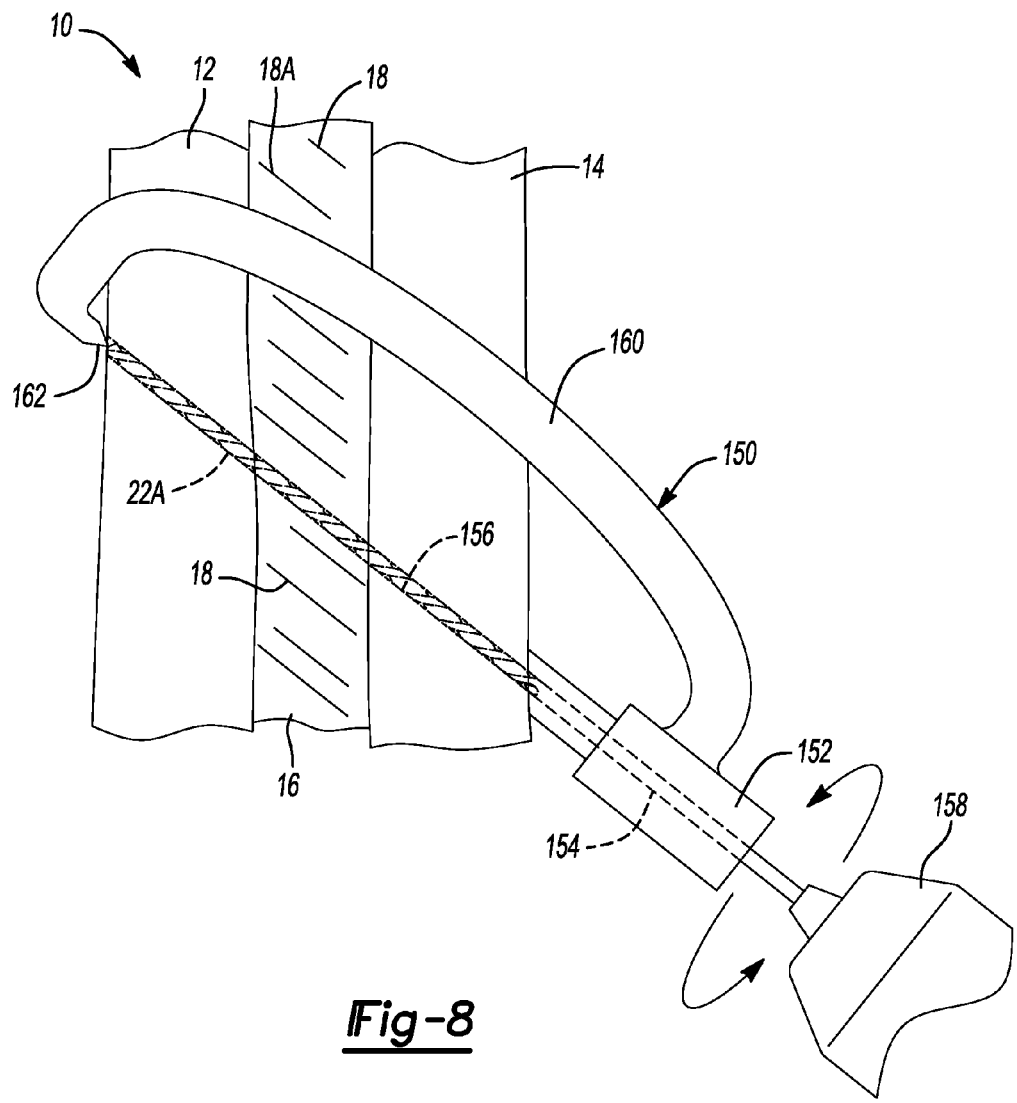
FIG. 8 illustrates a guide mounted to a forearm and preparation of the forearm to receive a suture.

With additional reference to FIG. 8, implantation of the suture 50A in the forearm 10 will be described. The first bore 22A can be drilled using any suitable guide, such as first drill guide 150. The first drill guide 150 generally includes a body 152 that defines a through hole 154 configured to receive a suitable cutting implement, such as drill bit 156 of a drill 158. Extending from the body 152 is a guide arm 160 sized and configured to span the forearm 10. At an end of the guide arm 160 opposite to the body 152 is a guide pin 162 that is suitable to engage an opposite side of the forearm 10 to assist in stabilizing the first drill guide 150 on the forearm 10.

The first drill guide 150 is orientated such that the through hole 154 is aligned parallel to the fibers 18 of the second group of interosseous fibers 18A. The drill 158 is positioned such that the drill bit 156 extends through the through hole 154 to engage the ulna 14. The drill 158 is then activated to drill the first bore 22A through the ulna 14, past the interosseous membrane 16, and through the radius 12. Drilling the first bore 22A past the interosseous membrane 16 can include through the interosseous membrane. The first drill guide 150 can be oriented in the opposite direction illustrated in FIG. 8, such that the body 152 abuts the radius 12 and the guide pin 162 abuts the ulna 14. The drill guide 150 can also be used to drill any of the other bores 22B-22E, as one skilled in the art will recognize.

Figure 9:
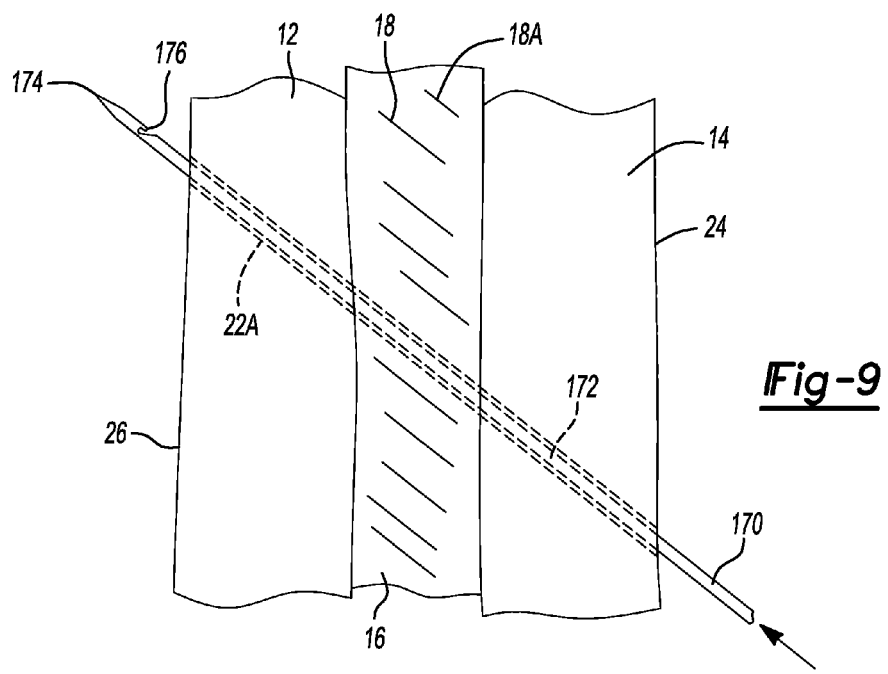
FIG. 9 illustrates an insertion pin extending through a bore formed in the forearm with the guide of FIG. 8.
Figure 10:
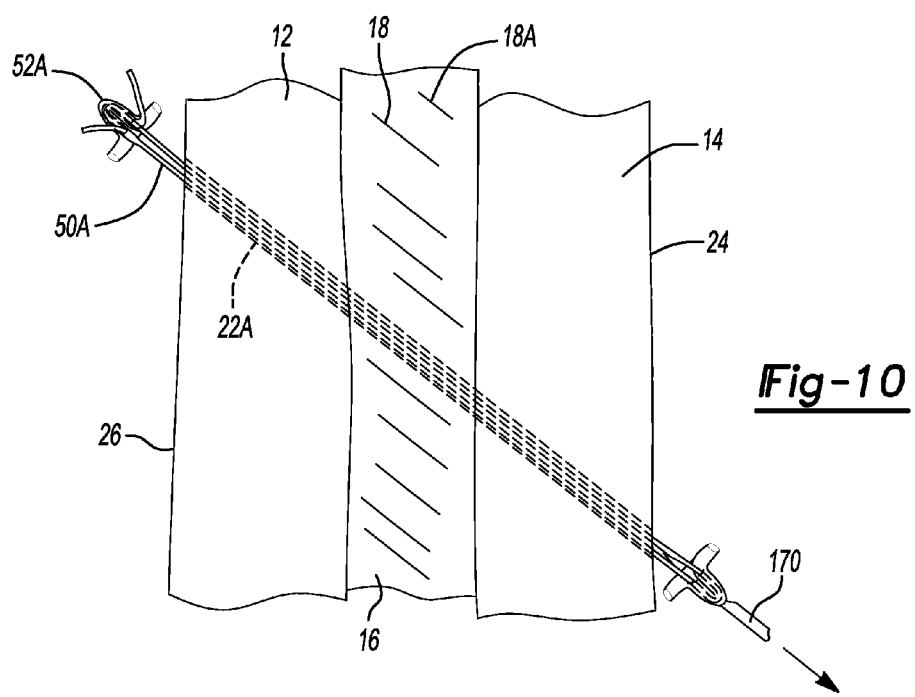
FIG. 10 illustrates the suture of FIG. 2 pulled through the bore formed in the forearm with the insertion pin.

With additional reference to FIG. 9, a pin 170 can be used to guide the suture 50A through the first bore 22A and assist in initially stabilizing the radius 12 in relation to the ulna 14. The pin 170 includes an elongated shaft 172, a pointed distal end 174, and a hook 176 proximate to the distal end 174. The pin 170 is inserted through the first bore 22A such that the pointed distal end 174 and hook 176 of the pin 170 exit the forearm 10 through the radius 12. With additional reference to FIG. 10, the guide pin 162 hooks the suture 50A to pull the suture 50A into the first bore 22A. With the suture 50A seated within the first bore 22A such that the first anchor 52A is at an outer surface 26 of the radius 12 and the second anchor 52B is at the outer surface 24 of the ulna 14, the first end 56 and the second end 58 of the suture strand 54 are pulled to tighten and adjustably compress the first and second anchors 52A and 52B against the radius 12 and the ulna 14 respectively, as illustrated in FIG. 11.

With additional reference to FIG. 12, a second drill guide is generally illustrated at reference numeral 210. The drill guide 210 includes a body 212 with a bone engaging surface 214. The bone engaging surface 214 is generally planar and includes a plurality of bone engagement teeth 216, which are pointed to facilitate secure engagement with either the radius 12 or the ulna 14. The second drill guide 210 defines a first through hole 218 and a second through hole 220. The first through hole 218 includes a first center axis C that is generally oblique to the bone engaging surface 214. The second through hole 220 includes a second center axis D that is generally perpendicular to a plane defined by the planar bone engaging surface 214. The first center axis C is orientated at an angle b, which is about 5° to about 55° relative to the second center axis D, such as about 20° to about 25° or about 40° to about 45°.

The angle b between the first center axis C and the second center axis D can be any suitable angle corresponding to the desired orientation of bores to be drilled in the forearm 10. For example, to drill the first bore 22E and the second bore 22E' as illustrated in FIG. 1B, the first through hole 218 will be angled from the second through hole 220 at an angle that corresponds to an angle at which the first bore 22E is to be angled from the second bore 22E', such as at an angle of from about 5° to about 55°, such as about 20° to about 25° or about 40° to about 45°. Thus, the second drill guide 210 can be used to form the first and second bores 22E and 22E' respectively for use in providing at least the following two different types of forearm stability: 1) stability along the longitudinal axis A provided by the second portion 50E" of the suture 50E extending through the second bore 22E' to prevent the radius 12 from moving relative to the ulna 14 perpendicular to the longitudinal axis A; and 2) load transfer stability, as well as natural range of motion during pronation and supination, provided by the first portion 50E' of the suture 50E extending through the first bore 22E.

With additional reference to FIG. 13, a pin guide is generally illustrated at reference numeral 250. The pin guide 250 generally includes a body 252 and a planar bone engaging surface 254. The body 252 generally defines a hemispherical guide surface 256. The planar bone engaging surface 254 includes a plurality of fixation members 258 that are sharpened and protrude from the bone engaging surface 254. The fixation members 258 can engage either the radius 12 or the ulna 14 to affix the pin guide 250 thereto.

With additional reference to FIGS. 14A and 14B, the second drill guide 210 can be used to drill, for example, the first bore 22E and the second bore 22E' to receive the suture 50E. The second drill guide 210 is mounted to the outer surface 24 of the ulna 14 such that the bone engagement surface 214 contacts the outer surface 24 and the bone engagement teeth 216 are pressed into and through the outer surface 24. The drill bit 156 is inserted through the first through hole 218 and rotated by the drill 158 to form the first bore 22E. The drill bit 156 is inserted through the second through hole 220 and rotated by the drill 158 to form the second bore 22E'.

Figure 15:
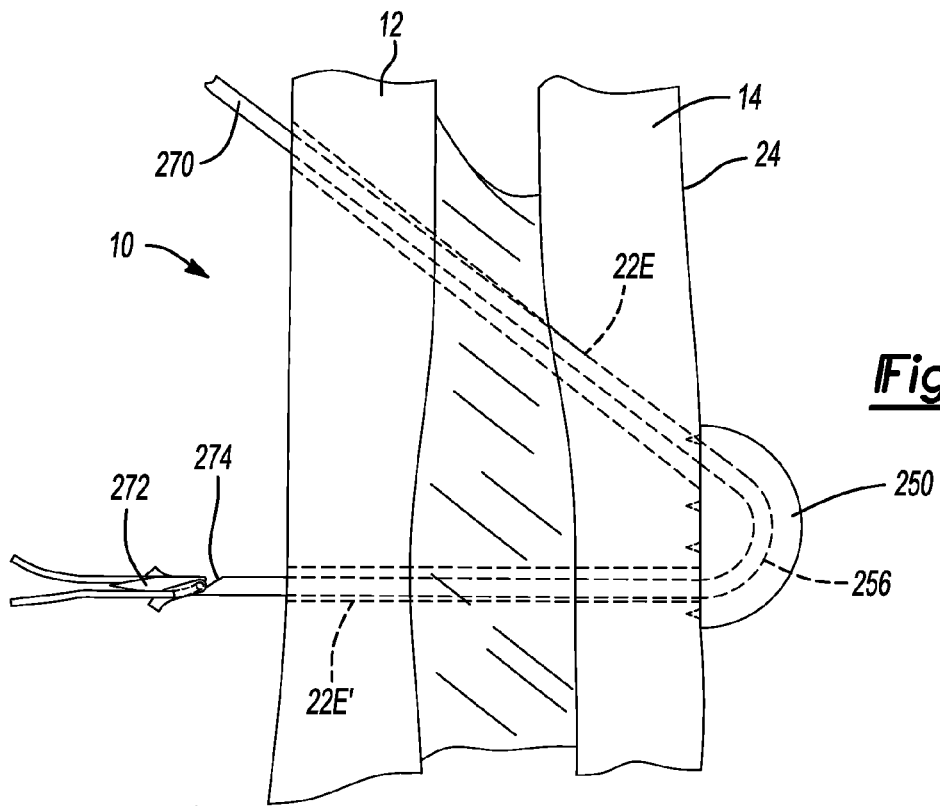
FIG. 15 illustrates the pin guide of FIG. 13 mounted to the forearm, the pin guide configured to guide a flexible guide pin through bores formed in the forearm using the drill guide.
Figure 16:
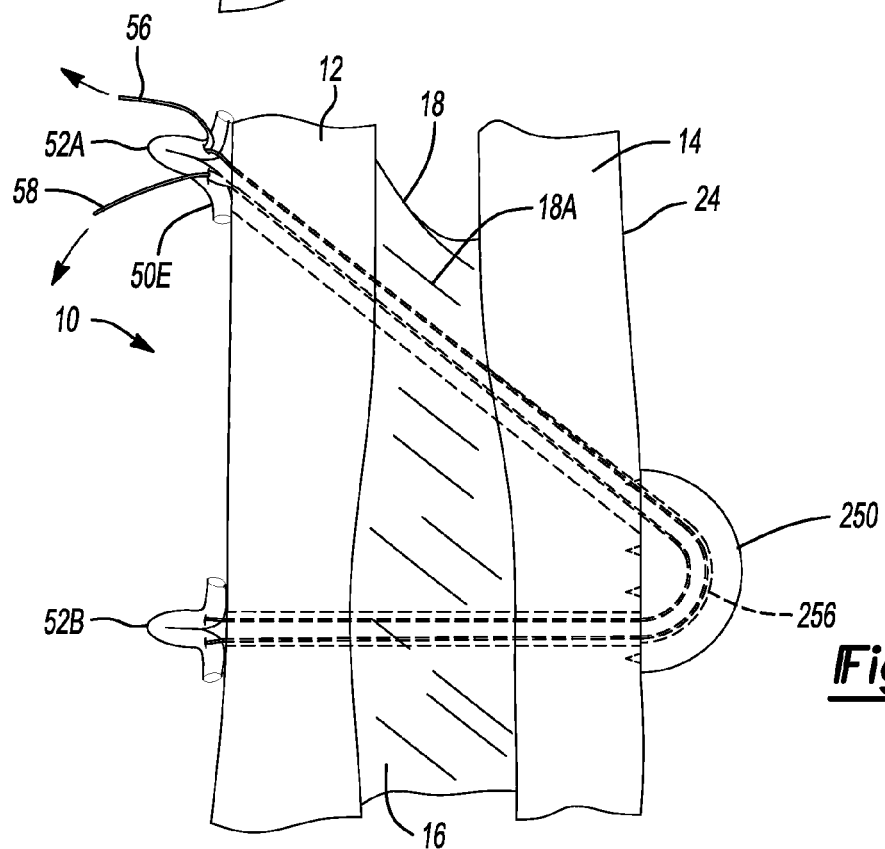
FIG. 16 illustrates the suture of FIG. 2 seated within the bores formed using the drill guide and fastened to the forearm.

With reference to FIGS. 15 and 16, after the first bore 22E and the second bore 22E' have been drilled, the pin guide 250 can be mounted to the outer surface 24 of the ulna 14 such that the pin guide 250 is aligned with the first bore 22E and the second bore 22E'. To position the suture 50E in the first and second bores 22E and 22E', a flexible guide pin 270 can be used, but is optional as one skilled in the art will recognize that the suture can be guided through the first and second bores 22E and 22E' in any suitable manner, such as without a guide. The flexible guide pin 270 includes a pointed distal end 272 and a hook 274 proximate to the pointed distal end 272. The flexible guide pin 270 is inserted into the first bore 22E at the radius 12 and pushed through the first bore 22E such that it reaches the pin guide 250. The pin guide 250 contacts the hemispherical guide surface 256, which directs the pointed distal end 272 of the flexible guide pin 270 into the second bore 22E'. As illustrated in FIG. 15, the flexible guide pin 270 then is pushed through the second bore 22E and exits the second bore 22E' at the outer surface 26 of the radius 12. The suture 50E is connected to the hook 274 and the flexible guide pin 270 is then pulled back through the second bore 22E' and the first bore 22E to position the suture 50E in both the first bore 22E and the second bore 22E', as illustrated in FIG. 16. With further reference to FIG. 16, the first end 56 and the second end 58 of the suture strand 54 are pulled to secure the suture 50E in the forearm 10. Rather than a single suture 50E extending through both the first bore 22E and the second bore 22E', separate sutures can be secured within each of the first bore 22E and the second bore 22E'.

Any two or more of the following can be provided in a kit: the first drill guide 150, the guide pin 170, the second drill guide 210, the pin guide 250, or flexible guide pin 270, each of which may be included in the kit in a plurality of different sizes and/or shapes. The kit may also include one or more of the sutures 50, as well as any of the other sutures described herein or incorporated by reference, or any other suitable fastening device.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for repairing a defect in an interosseous membrane located between a first bone and a second bone comprising:
    coupling a flexible member to the first bone and the second bone, the flexible member extending past a first area of the interosseous membrane between the first bone and the second bone; and
    orienting the flexible member such that the flexible member extends generally parallel to fibers of the first area of the interosseous membrane.

2. The method of claim 1, wherein the first bone is a radius and the second bone is an ulna, and the flexible member extends through the interosseous membrane.

3. The method of claim 1, further comprising anchoring the flexible member to the first bone with a first anchor and anchoring the flexible member to the second bone with a second anchor.

4. The method of claim 1, further comprising coupling a first portion of the flexible member to the first bone and the second bone, the first portion of the flexible member extending past the first area of the interosseous membrane generally parallel to the fibers of the first area of the interosseous membrane; and
    coupling a second portion of the flexible member to the first bone and the second bone, the second portion of the flexible member extending past the first area of the interosseous membrane.

5. The method of claim 4, further comprising coupling the first portion of the flexible member to the first bone with a first anchor and coupling the second portion of the flexible member to the first bone with a second anchor;
    wherein the first portion of the flexible member extends through the first area of the interosseous membrane and the second portion of the flexible member extends through a second area of the interosseous membrane.

6. The method of claim 4, wherein the second portion of the flexible member extends generally through the first area perpendicular to a longitudinal axis of the interosseous membrane.

7. The method of claim 1, further comprising drilling a bore that extends through the first bone, past the first area of the interosseous membrane, and through the second bone, the bore is orientated such that it extends generally parallel to fibers of the first area of the interosseous membrane; and
    inserting the flexible member through the bore prior to coupling the flexible member to the first bone and the second bone, the flexible member is threaded through the bore with a pin, cooperation between the flexible member and the pin is provided with a hook of the pin.

8. The method of claim 1, wherein the flexible member is a self-locking suture construct including a braided suture with a sleeve portion that defines a first opening and a second opening, a first end of the braided suture extends through both the first opening and the second opening, and a second end of the braided suture extends through both the first opening and the second opening.

9. A method for repairing a defect in an interosseous membrane located between a first bone and a second bone comprising:
    orienting a first suture portion such that the first suture portion extends generally parallel to fibers of a first area of the interosseous membrane;
    coupling the first suture portion to the first bone and the second bone, the first suture portion extending past the first area of the interosseous membrane between the first bone and the second bone; and
    coupling a second suture portion to the first bone and the second bone, the second suture portion extending past the first area of the interosseous membrane between the first bone and the second bone.

10. The method of claim 9, further comprising orienting the second suture portion such that the second suture portion extends generally perpendicular to a longitudinal axis of the interosseous membrane, coupling the first suture portion such that it extends through the first area of the interosseous membrane, and coupling the second suture portion such that it extends through the first area of the interosseous membrane.

11. The method of claim 9, further comprising orienting a third suture portion such that the third suture portion extends generally parallel to fibers of a second area of the interosseous membrane and extends generally oblique to fibers of the first area of the interosseous membrane; and
    coupling the third suture portion to the first bone and the second bone, the third suture portion extending past the second area of the interosseous membrane between the first bone and the second bone.

12. The method of claim 9, further comprising coupling the first suture portion to the first bone with an anchor seated on an exterior surface of the first bone, a first end of the suture portion and a second end of the suture portion are pulled to tension the first suture portion and tighten the first suture portion against the first bone.

13. The method of claim 9, further comprising coupling the first suture portion to the first bone with an anchor recessed within an exterior surface of the first bone.

14. The method of claim 9, further comprising coupling the first suture portion to the first bone with a soft, self-locking anchor.

15. The method of claim 9, further comprising coupling the first suture portion to the first bone with a rigid anchor.

16. The method of claim 9, further comprising:
    positioning a first drill guide on the first bone to drill a first hole and a second hole in each of the first bone, the interosseous membrane, and the second bone;
    positioning a second guide on the first bone to guide one flexible pin through both the first hole and the second hole; and
    inserting the first suture portion through the first hole and the second suture portion through the second hole.

17. The method of claim 9, wherein the first suture portion and the second suture portion are each included in a single suture.

18. The method of claim 9, wherein the first suture portion and the second suture portion are each included on different sutures.

* * * * *

UNITED STATES PATENT AND TRADEMARK OFFICE
CERTIFICATE OF CORRECTION

PATENT NO. : 8,506,597 B2  
APPLICATION NO. : 13/281016  
DATED : August 13, 2013  
INVENTOR(S) : Ryan A. Kaiser et al.

Page 1 of 1

It is certified that error appears in the above-identified patent and that said Letters Patent is hereby corrected as shown below:

On Title Page 12, Column 1, Item (56) Other Publications, Line 12, Delete "paages" and insert -- pages --

In the Claims

Column 9, Claim 4, Line 51, after "past", delete "the first area of"

Signed and Sealed this
Eleventh Day of November, 2014

Michelle K. Lee
*Deputy Director of the United States Patent and Trademark Office*